United States Patent
Heindl et al.

(10) Patent No.: US 7,759,470 B2
(45) Date of Patent: Jul. 20, 2010

(54) LABELING REAGENT

(75) Inventors: Dieter Heindl, Paehl (DE); Frank Bergmann, Iffeldorf (DE); Hans-Peter Josel, Weilheim (DE); Dirk Kessler, Peiting (DE); Gunter Lampert, Paehl (DE); Christian Weilke, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/707,399

(22) Filed: Feb. 16, 2007

(65) Prior Publication Data

US 2007/0196852 A1 Aug. 23, 2007

(30) Foreign Application Priority Data

Feb. 20, 2006 (EP) .................................. 06003366

(51) Int. Cl.
*C07G 3/00* (2006.01)
*C07H 21/02* (2006.01)
*C07H 21/04* (2006.01)
*C07H 19/04* (2006.01)
*C12Q 1/68* (2006.01)

(52) U.S. Cl. ...................... 536/4.1; 536/23.1; 536/24.3; 536/25.3; 536/26.6; 435/6

(58) Field of Classification Search ................... 536/4.1, 536/23.1, 25.3, 24.3, 26.6; 435/6
See application file for complete search history.

(56) References Cited

U.S. PATENT DOCUMENTS 5,451,463 A 9/1995 Nelson et al.
2005/0147976 A1 7/2005 Su

FOREIGN PATENT DOCUMENTS

| EP | 01313219 B1 | 4/1989 |
| EP | 0135587 B1 | 5/1990 |
| EP | 0954606 B1 | 11/1999 |
| WO | WO9211388 A1 | 7/1992 |
| WO | WO9743451 A1 | 11/1997 |

OTHER PUBLICATIONS

Wojczewski, et al., "Fluorescent Oligonucleotides—Versatile Tools as Probes and Primers for DNA and RNA Analysis", Synlett 1999, No. 10, 1667-1678.
Goodchild, J., "Conjugates of Oligonucleotides and Modified Oligonucleotides: A Review of Their Synthesis and Properties", 6148 Bioconjugate Chemistry 1 (1990), May/June, No. 3, Washington, DC.
Smith, C. et al., "Use of 5-Nitroindole-2'-Deoxyribose-5'-Triphosphate for Labelling and Detection of Oligonucleotides", Nucleosides & Nucleotides, 17(1-3), 555-564 (1998).

*Primary Examiner*—Jezia Riley
(74) *Attorney, Agent, or Firm*—Marilyn L. Amick; Roche Diagnostics Operations, Inc.

(57) ABSTRACT

The current invention restates substituted indole nucleosides as both terminal as well as internal building blocks of labeled oligonucleotide probes for the detection, analysis and quantitation of nucleic acids. The substituent comprises a linker and a detectable group or a linker and a reactive group for post synthesis coupling. These modified nucleosides grant access to a wide application area. These new substituted indole nucleosides can be used as labeling reagents for the facile preparation of e.g. optimized hybridization probes, Taqman-probes, or molecular beacon probes.

12 Claims, 4 Drawing Sheets

LABELING REAGENT

RELATED APPLICATIONS

This application claims priority to EP 06003366.9 filed Feb. 20, 2006.

FIELD OF THE INVENTION

The current invention restates substituted indole nucleosides as both, terminal as well as internal building blocks of labeled oligonucleotide probes for the detection, analysis and quantification of nucleic acids. The substituent comprises a linker and a detectable group or a linker and a reactive group for post synthesis labeling. These modified nucleosides grant access to a wide application area. These new substituted indole nucleosides can be used as labeling reagents for the facile preparation of e.g. optimized hybridization probes, Taqman-probes or molecular beacon probes.

BACKGROUND OF THE INVENTION

The steady increase in the number of decoded and mapped genomic sequences from flora and fauna is an impressive demonstration how important DNA-techniques are nowadays. But not the mere sequencing of DNA is of importance. With increasing knowledge in the field of genomics and proteomics, the impact of specific effects, e.g. mutations, on the future of cells or organisms comes into the focus of scientists. Since on the one hand, the nucleic acids are often present in very small concentrations and, on the other hand, they are often found in the presence of many other solid and/or dissolved substances, e.g. after lysis of cells, they are difficult to isolate or to measure.

Diverse methods for the detection, analysis and quantitation by hybridization of the target nucleic acid with a detectable probe have been established, e.g., Southern hybridization, dot blotting, gel-assays, or PCR.

The main tool of nucleic acid related work, e.g. for amplification of polymeric nucleic acids, is the polymerase chain reaction (PCR). In recent years the knowledge about and the applications of PCR were noticeably expanded.

A PCR procedure consists in general of three steps: sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. The concurrent amplification and analysis of the sample within the same tube without changing the instrument reduces sample handling time, and minimizes the risk of product contamination for subsequent reactions. This approach of combining amplification with analysis has become known as "real time" PCR (U.S. Pat. No. 6,174,670).

Other possible amplification reactions are the ligase chain reaction (LCR, Wu, D. Y., and Wallace, R. B., Genomics 4 (1989) 560-569; Barany, F., Proc. Natl. Acad. Sci. USA 88 (1991) 189-193; U.S. Pat. No. 5,494,810); Polymerase Ligase Chain Reaction (Barany, F., PCR Methods Appl. 1 (1991) 5-16); Gap-LCR (WO 90/01069; U.S. Pat. No. 6,004, 286); Repair Chain Reaction (EP 0 439 182 A2); 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; WO 92/08808); and NASBA (U.S. Pat. No. 5,130,238). Further, there are strand displacement amplification (SDA, U.S. Pat. No. 5,270,184; U.S. Pat. No. 5,455,166), transcription mediated amplification (TMA) and Q-beta-amplification (for a review see e.g. Whelen, A. C., and Persing, D. H., Annu. Rev. Microbiol. 50 (1996) 349-373; Abramson, R. D., and Myers, T. W., Curr. Opin. Biotechnol. 4 (1993) 41-47) as well as isothermal and chimeric primer-initiated amplification of nucleic acids (ICAN, Shimada, M., et al., Rinsho Byori. 51 (2003) 1061-1067) and cascade rolling circle amplification (CRCA, Thomas, D. C., et al., Arch. Pathol. Lab. Med. 123 (1999) 1170-1176).

For the above mentioned nucleic acid technique synthetic (deoxy)-oligonucleotides which have been provided with a detectable label are necessary, e.g. to carry out a broad spectrum of diverse molecular biological and molecular diagnostic methods.

Methods for the synthesis of single stranded oligonucleotide and oligonucleotide analogue sequences are known from the art (e.g. Oligonucleotide Synthesis: A Practical Approach, Gait, ed., IRL Press, Oxford (1984); Kuijpers, W. H. A., et al., Nucleic Acids Research 18 (1990) 5197-5205; Dueholm, K. L., J. Org. Chem. 59 (1994) 5767-5773; Agrawal, S. (ed.), Methods in Molecular Biology, volume 20).

The first effective and widely applicable method for the synthesis of oligo- and polynucleotides was the phosphotriester method (see e.g. Letsinger, R. L., et al., J. Am. Chem. Soc. 91 (1969) 3360-3365). To prevent side reactions like branching during the synthesis, reactive groups were protected with, e.g., the beta-cyanoethyl group or the ortho-chlorophenyl group. As activator for the coupling step mesityl sulfonyl chloride and mesityl sulfonyl nitrotriazole have been used.

Synthetic (deoxy-)oligonucleotides are usually prepared on a solid phase with the aid of phosphoramidite chemistry. Glass beads having pores of a defined size (abbreviated in the following as CPG=controlled pore glass) are usually used as the solid phase. The first monomer is bound to the support via a cleavable group such that the oligonucleotide can be set free by cleavage of this group after the solid phase synthesis is completed. The first monomer additionally contains a protected hydroxyl group, whereas dimethoxytrityl (DMTr) is usually utilized as the protective group. The protective group can be removed by acid treatment. Then 3'-phosphoramidite derivatives of (deoxy-)ribonucleosides that are also provided with a DMTr protective group are coupled in a cyclic process to each successive reactive group after is has been freed of the DMTr protective group.

According to the prior art trifunctional support materials can be used to prepare oligonucleotides that are labeled at the 3' end. For this a trifunctional spacer with two reactive hydroxyl groups and an additional reactive group, preferably an amino group, is provided. The detectable label is attached to the reactive amino group of the trifunctional spacer. However, alternatively the detectable label is not only coupled to the trifunctional spacer via a reactive amino group but also via a third hydroxyl group or an SH group (U.S. Pat. No. 5,451, 463; WO 92/11388). In a third step the trifunctional spacer is bound via its hydroxyl group that is still free to the linking group of the solid phase material that is provided with a cleavable bond.

Alternatively the detectable label is not coupled until the actual oligonucleotide synthesis (U.S. Pat. No. 5,141,837). However, since this requires multiple independent coupling reactions, such a production process is laborious, costly and cannot be automated.

Labeled phosphoramidites in which the marker group is linked to the phosphoramidite via a $C_3$-$C_{12}$ linker are usually used to synthesize oligonucleotides labeled at the 5' end.

Hence detectable labels can also be introduced internally by the phosphoramidite strategy (Wojczewski, C., et al., Synlett 10 (1999) 1667-1678). The same trifunctional spacers can be used for this as for the synthesis of CPG materials. Instead of binding one of the hydroxyl groups to the solid phase, this hydroxyl group is converted into a phosphoramnidite in this process. The resulting phosphoramidite can be used for oligonucleotide synthesis like a standard amidite. In principle such phosphoramidites can also be used for internal labeling by replacing a standard nucleoside phosphoramidite by a fluorophore-labeled phosphoramidite during the synthesis cycle. However, it is preferably used for 5' labeling since internal labeling interrupts the base pairing in the strand.

Oligonucleotides provided with a fluorescent label such as fluorescein are often used in molecular biology, such as for the real-time measurement of PCR reactions (WO 97/46707). The fluorescent dyes can be coupled to, e.g., the amino group of the trifunctional spacer in different ways according to the prior art.

On the one hand the fluorescent dye is introduced as isothiocyanate which reacts with the amino group of a linker or the nucleobase to form a thiourea bond. In an alternative process the N-hydroxy-succinimide ester (NHS-ester) of a fluorophore-carboxylic acid is reacted with the free amino group of the spacer to form an amide bond. Alternatively the linker is-terminated with a carboxyl group and is then reacted with an aminomodified label.

Beside these chemical methods for the preparation of labeled oligonucleotides enzymatic methods are known. For example, a terminal label can be introduced using the enzyme terminal deoxynucleotidyl transferase which introduces an additional nucleotide at the end of an existing polydeoxynucleotide chain. This enzymatically introduced nucleotide bears the signal entity (see e.g. EP 0 122 614).

The great success of real-time methods is closely linked to the detection or change of a reporter signal. This signal change evolves from the interaction of the probe molecule with the target molecule.

Monitoring fluorescence during each cycle of PCR initially involved the use of ethidium bromide. (Higuchi, R., et al., Bio/Technology 10 (1992) 413-417; Higuchi R., et al., Bio/Technology 11 (1993) 1026-1030; U.S. Pat. No. 5,994,056). In that system fluorescence is measured once per cycle as a relative measure of product concentration. Ethidium bromide detects double stranded DNA; if the template is present, fluorescence intensity increases with temperature cycling. Other fluorescent systems have been developed that are capable of providing additional data concerning the nucleic acid concentration and sequence.

In kinetic real time PCR, the formation of PCR products is monitored in each cycle of the PCR. The amplification is usually measured in thermocyclers which have additional devices for measuring fluorescence signals during the amplification reaction. In general, there exist different formats for real time detection of amplified DNA, of which the following are well known and commonly used in the art:

DNA binding dye format: Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like Sybr Green I, for example, do not affect the efficiency of the PCR reaction (U.S. Pat. No. 6,174,670).

All other formats known in the art require the design of a fluorescent labeled hybridization probe which only emits fluorescence upon binding to its target nucleic acid.

Taqman probe: A single-stranded hybridization probe is labeled with two components. When the first component is excited with light of a suitable wavelength, the absorbed energy is transferred to the second component, the so-called quencher, according to the principle of fluorescence resonance energy transfer (FRET). During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured (U.S. Pat. No. 5,538,848).

Molecular Beacons: These hybridization probes are also labeled with a first component and with a second quencher component; the labels preferably being located at both ends of the probe. As a result of the secondary structure of the probe, both components are in spatial vicinity in solution. After hybridization to the target nucleic acids both components are-separated from one another such that after excitation with light of a suitable wavelength the fluorescence emission of the first component can be measured (U.S. Pat. No. 5,118,801).

FRET hybridization probes: The FRET hybridization probe test format is especially useful for all kinds of homogenous hybridization assays (Matthews, J. A., and Kricka, L. J., Anal. Biochem. 169 (1988) 1-25). It is characterized by a pair of two single-stranded hybridization probes, which are used simultaneously and which are complementary to adjacent sites of the same strand of the amplified target nucleic acid. Both probes are labeled with different fluorescent components. When excited with light of a suitable wavelength, the first component transfers the absorbed energy to the second component according to the principle of fluorescence resonance energy transfer in a way that a fluorescence emission of the second component can be measured when both hybridization probes bind to adjacent positions of the target molecule to be detected.

When annealed to the target sequence, the hybridization probes must sit very close to each other, in a head to tail arrangement. Usually, the gap between the labeled 3' end of the first probe and the labeled 5' end or the second probe is as small as possible, i.e. 1-5 bases. This allows for a close vicinity of the FRET donor and the FRET acceptor compound.

Besides PCR and real time PCR, FRET hybridization probes and molecular beacons are used for melting curve analysis. In such an assay, the target nucleic acid is amplified first in a typical PCR reaction with suitable amplification primers. The hybridization probes may already be present during the amplification reaction or added subsequently. After completion of the PCR-reaction, the temperature of the sample is constitutively increased, and fluorescence is detected as long as the hybridization probe is bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed. Alternatively it is possible to use a fluorescent-labeled primer and only one labeled oligonucleotide probe (Bernard, P.S., et al., Anal. Biochem. 235 (1998) 101-107).

Single Label Probe (SLP) Format: This detection format consists of a single oligonucleotide labeled with a single fluorescent dye at either the 5'- or 3'-end (WO 02/14555). Two different designs can be used for oligonucleotide labeling:

G-Quenching Probes and Nitroindole-dequenching probes.

In the G-Quenching embodiment, the fluorescent dye is attached to a C at the 5'- or 3'-end of the oligonucleotide. In case two G's are located on the target strand opposite to C and in position 1 aside of complementary oligonucleotide probe, fluorescence decreases significantly when the probe is hybridized to the target.

In the Nitroindole dequenching embodiment, the fluorescent dye is attached to nitroindole at the 5'- or 3'-end of the oligonucleotide. Nitroindole decreases the fluorescent signaling of the free probe. Fluorescence increases when the probe is hybridized to the target DNA due to a dequenching effect.

In US patent application US 2003/0022177 Wittwer et al. principally introduced base analogs for the modification of the terminal ends of probe oligonucleotides.

PCR products can be quantified in two fundamentally different ways.

End point determination of the amount of PCR product formed in the plateau phase of the amplification reaction: In this case the amount of PCR product formed does not correlate with the amount of the initial copy number since the amplification of nucleic acids at the end of the reaction is no longer exponential and instead saturation is reached. Consequently different initial copy numbers exhibit identical amounts of PCR product formed. Therefore the competitive PCR or competitive RT-PCR method is usually used in this procedure. In these methods the specific target sequence is coamplified together with a dilution series of an internal standard of a known copy number. The initial copy number of the target sequence is extrapolated from the mixture containing an identical PCR product quantity of standard and target sequence (Zimmermann, K., and Mannhalter, J. W., BioTechniques 21 (1996) 280-279). A disadvantage of this method is also that measurement occurs in the saturation region of the amplification reaction.

Kinetic real-time quantification in the exponential phase of PCR: In this case the formation of PCR products is monitored in each cycle of the PCR. The amplification is usually measured in thermocyclers which have additional devices for measuring fluorescence signals during the amplification reaction. A typical example of this is the Roche Diagnostics LightCycler (Cat. No. 2 0110468). The amplification products are, for example, detected by means of fluorescent labeled hybridization probes, which only emit fluorescence signals when they are bound to the target nucleic acid, or in certain cases also by means of fluorescent dyes that bind to double-stranded DNA. A defined signal threshold is determined for all reactions to be analyzed and the number of cycles required to reach this threshold value is determined for the target nucleic acid as well as for the reference nucleic acids such as the standard or housekeeping gene. The absolute or relative copy numbers of the target molecule can be determined on the basis of these values obtained for the target nucleic acid and the reference nucleic acid (Gibson, U. E., et al., Genome Res. 6 (1996) 995-1001; Bieche, I., et al., Cancer Res. 59 (1999) 2759-2765; WO 97/46707; WO 97/46712; WO 97/46714). Such methods are also referred to as real-time PCR.

For synthesizing nucleic acid probes several compounds and their use for incorporation as monomeric units into nucleic acids are known in the art. Such compounds provide functional groups and/or linking moieties for the covalent attachment of reporter groups or labels. In the course of the chemical synthesis of the oligomeric compound, the skeletal structure of the "non-nucleotide compound" or "modified nucleotide" is connected with the "oligonucleotide" backbone, for example by phosphoramidite-based chemistry resulting in a phosphodiester bond. A given incorporated compound thus represents a "modified nucleotide" within the newly generated "modified oligonucleotide". A label is bound via a functional group, e.g. on a "linking moiety", exemplified by, but not limited to, an amino function that is present on the skeletal structure or on a "linking moiety", which connects the skeleton with the functional group. A label can be attached covalently to the compound prior to or after the synthesis of a "modified oligonucleotide", upon the removal of an, optional, protecting group from the functional group to which the label is to be coupled.

EP 0 135 587 reports modifications of conventional nucleosides which carry a reporter group attached to a substituent group of the nucleotide base. EP 0 313 219 reports non-nucleoside reagents characterized by a linear hydrocarbon skeletal structure with a linking moiety or a side group to which a label can be bound. EP 0 313 219 does not report other types of skeletal structures and their particular properties.

U.S. Pat. No. 5,451,463 reports trifunctional non-nucleotide reagents, particularly 1,3-diol-based skeletal structures possessing a primary amino group. Such reagents can be used, for example, for terminal labeling of the 3' terminus of oligonucleotides. WO 97/43451 reports non-nucleotide reagents based on a carbocyclic ($C_5$ to $C_7$) skeletal structure.

In summary, these technologies are either based on non-nucleosidic linkers, which upon internally incorporation result in disruption of the probe structure and base pairing, or on modifications of a specific nucleobase, which requires for flexible internal labeling the synthesis of four different phosphoramidites.

Thus, it was the object of the present invention to overcome the afore described problems by providing an alternate labeling system which allows for an easy as well as position and dye independent labeling. In another aspect, the objective of the present invention was to provide improved probes for nucleic acid amplification, detection and quantitation.

SUMMARY OF THE INVENTION

Thus, the invention is directed to a new, detectable compound for nucleic acid probe labeling. The compound comprises a nucleoside with a modified indole as nucleobase. This nucleoside shows improved synthetic and detection properties.

More precisely, the invention comprises the synthesis and use of a nucleoside with a 3-substituted methanesulfonylamino indole as nucleobase. By incorporating this nucleoside into an oligonucleotide, terminal, as well as, internal labeling can be accomplished. Therefore a position independent labeling of oligonucleotides and, consequently, of PCR probes can be carried out.

This nucleoside can be incorporated at any position of an oligonucleotide. Thus in case of a dye stable during oligonucleotide synthesis, no post synthesis labeling is required. Some dyes have to be protected to be compatible with oligonucleotide synthesis e.g. fluorescein hydroxyl groups are pivaloyl protected. Additionally, for dyes unstable during oligonucleotide synthesis, a reactive group can be attached to the indole based nucleobase for post-synthesis labeling.

The present invention comprises compounds having the Formula I

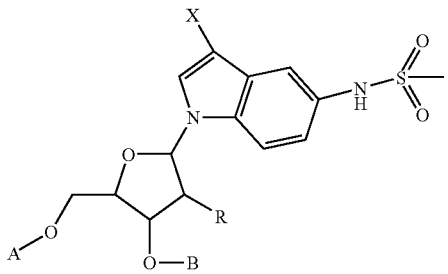

Formula I characterized in that

A and B are independent from each other and independent from R and X, and whereby A and B are selected from the group consisting of hydrogen, a protecting group, a solid phase with a linker, a phosphoramidite, a H-phosphonate, a triphosphate, a phosphate, and a chain of nucleotide residues, with the proviso that A but not B is a triphosphate, with the proviso that if one of A or B is a phosphoramidite or an H-phosphonate, the other of A and B is a protective group and R is not OH, with the proviso that only one of A and B is a solid phase with a linker, and whereby R=H, OH, O-alkyl, O-alkenyl, O-alkinyl, O-protective group, or F, and X is either a reactive group or a protected reactive group or a linker with a reactive group or a linker with a protected reactive group or a signal entity or a protected signal entity or a linker with a signal entity or a linker with a protected signal entity.

One embodiment of the current invention is an oligonucleotide comprising a compound of Formula I.

Another embodiment of the current invention is an oligonucleotide comprising at least two signal entities based on a compound of Formula I.

Another embodiment of the current invention is a labeling compound comprising a compound of Formula I, wherein B is either a phosphoramidate group, a H-phosphonate, or a CPG and A is a protective group.

Another embodiment of the current invention is a method of synthesizing an oligonucleotide comprising a compound of Formula I, comprising the step of incorporation of a labeling compound according to the invention during oligonucleotide synthesis.

Another embodiment of the current invention is a method of synthesizing an oligonucleotide comprising a compound of Formula I, comprising the steps of a) incorporating a labeling compound according to the invention during oligonucleotide synthesis, wherein said labeling compound contains a reactive group for coupling of a signal entity to said reactive group, and b) coupling of a signal entity to said reactive group.

In a further embodiment the compound of Formula I, incorporated into an oligonucleotide, comprises a signal entity.

In another embodiment an oligonucleotide, comprising a compound of Formula I, is used as a hybridization probe.

In another embodiment an oligonucleotide, comprising a compound of Formula I, is used as a member of one pair of FRET hybridization probes.

In another embodiment an oligonucleotide, comprising two compounds of Formula I, each with one signal entity, is used as a Taqman probe or Molecular Beacon probe.

DETAILED DESCRIPTION OF THE INVENTION

Figure 1A:
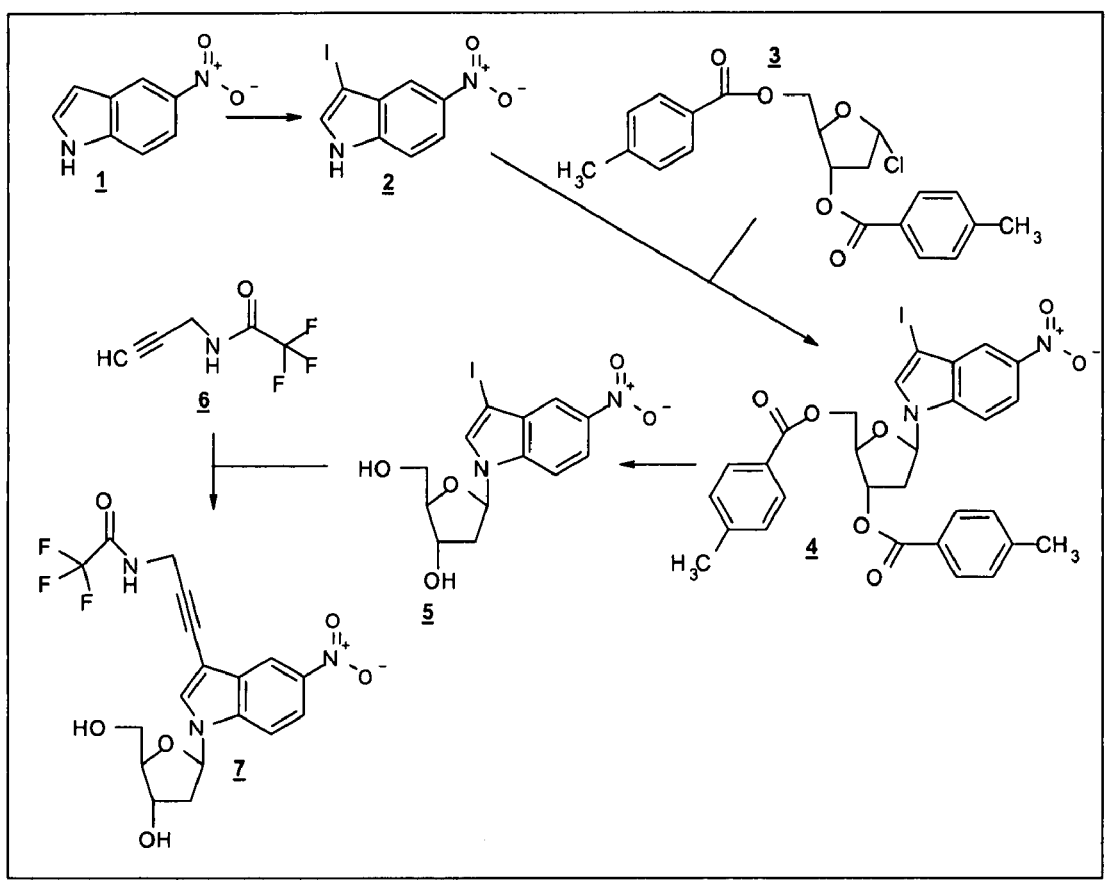
FIG. 1a: Synthetic route to a nucleoside with reactive group (1=5-Nitro-1H-indole; 2=3-Iodo-5-nitro-1H-indole; 3=5-chloro-2-(4-methyl-benzoyloxymethyl)-3-(4-methyl-benzoyloxy)-tetrahydro-furan; 4=5-(3-Iodo-5-nitro-indol-1-yl)-2-(4-methyl-benzoyloxymethyl)-3-(4-methyl-benzoyloxy)-tetrahydro-furan; 5=2-Hydroxymethyl-5-(3-iodo-5-nitro-indol-1-yl)-tetrahydro-furan-3-ol; 6=2,2,2-Trifluoro-N-prop-2-ynyl-acetamide; 7=2,2,2-Trifluoro-N-{3-[1-(4-hydroxy-5-hydroxymethyl-tetrahydro-furan-2-yl)-5-nitro-1H-indol-3-yl]-prop-2-ynyl}-acetamide)

The current invention is directed to a new detectable compound for nucleic acid probes. The compound comprises a nucleoside with a modified 3-substituted methanesulfonylamino indole as nucleobase. This nucleoside shows improved synthetic and detection properties.

Within the scope of the present invention some of the terms used are defined as follows:

An "oligonucleotide" is a linear oligomer of naturally occurring or modified monomeric subunits and consists of a sequence composed of two or more monomeric subunits. These subunits are referred to as nucleotides. An oligonucleotide is optionally derived from natural sources, but is often synthesized chemically. It is of any size.

The term "nucleotide" encompasses in connection with the present invention not only (deoxy-)oligo-ribonucleotides but also all back-bone modified oligonucleotides, as e.g. methylphosphonates or phosphothioates, all sugar modified oligonucleotides, as e.g. LNA, HNA, 2'-O-alkyl derivatives, and all base analogs, as e.g. 7-deazapurines, as well as chimeras comprising different types of nucleotides and analogues thereof.

An "oligonucleotide analogue" refers to a polymer with two or more monomeric subunits, wherein at least one of the monomers is not belonging to the group of the natural nucleotides A (adenine), T (thymine), C (cytosine), G (guanine), and U (uracil). This non-natural nucleotide has some structural features in common with a naturally occurring nucleotide which allows it to interact with naturally occurring nucleotides.

The expressions "chain of nucleotides" or "chain of nucleotide residues" which are used interchangeably within this application refer to a polymer with two or more monomeric subunits, wherein these subunits comprise nucleotides and modified nucleotides as defined above. The "chain of nucleotides" is of any size, preferably of 5 to 70 monomeric subunits and more preferably of 10 to 40 monomeric subunits.

A "nucleoside" is a glycoside, normally a pentose glycoside, in which the aglycone, normally a heterocyclic base, is connected to a sugar moiety, normally a pentose.

A "protecting group" is any of the groups that have been designed to block one reactive site in a molecule during a chemical reaction that is carried out at another reactive site of this molecule. The protecting groups of the herein described synthesis can optionally be any of those described in, e.g., Greene, et al., Protective Groups in Organic Chemistry, 2nd Ed., John Wiley & Sons, New York, N.Y., 1991.

A "labeled oligonucleotide" includes oligonucleotides having at least one label. The label may be a fluorescent label but can also be of any other kind. The oligonucleotide may contain the label in various ways, including linked to a base of the oligonucleotide, or the dye may be used to replace a base as part of a "virtual nucleotide" structure. If more than one label, which can be of the same or of different types, is attached to the oligonucleotide, at least one of the labels is attached via the chemistry according to the invention. The other label(s) may be attached by other methods known in the art.

"Complementary" refers to nucleic acid sequences that form a base-paired structure with each other. "Complementary" refers in the case of oligonucleotides to the opposing strand and when discussing individual bases of an oligonucleotide, "complementary" refers to the position or base on the opposing strand. "Generally complementary" sequences are two nucleic acid sequences that have at least 80% homology due to the degeneracy of the genetic code. Thus, such sequences may have mismatches but have sufficient homology to form base-paired structures with each other.

A "signal entity" or "detectable label" denotes a substance that can be detected with the aid of analytical methods. This can be, e.g., a substance that can be detected with the aid of spectroscopy (visible-, UV-, IR- or mass spectroscopy), immunological assays or with the aid of NMR. In particular, the term "detectable label" includes fluorescent dyes, such as fluoresceins, coumarines, oxazines, cyanines or rhodamines. Other labels included are quencher molecules, haptenes, biotin, ruthenium-labels, spin-labels, mass tags and non-linear-optic labels.

One but not exclusive class of signal entities are fluorescent labels (fluorescent dyes) such as coumarines, fluorescein and its derivatives (e.g. JOE, FAM, rhodamines, Alexa Fluor 488, Oregon Green dyes, erythrosines, eosins), fluorescein-cyanine conjugates (e.g. Big Dyes), derivatives of the bispyrromethene boron-difluoride dyes (e.g. BODIPY), cyanine monomers and dimers (e.g. TOTO, YOYO, TO-PRO, Cy3, Cy5, Cy5.5, Cy7, LCRed 705). Preferred fluorescent labels are coumarines and rhodamines. Other labels are, e.g., immobilization to distinguishable supports or linkage to biomolecules (e.g. biotin). Some labels require protection, if used directly in oligonucleotide synthesis, fluorescein, e.g., is protected as bispivaloate.

The term "linker" represents a chain of atoms. This chain of atoms has a length of from 1 to 30 atoms, preferred of from 4 to 20 atoms. The chain may contain single, double and/or triple bonds, and/or atoms which are part of a carbocycle, and/or may be substituted by alkyl-, alkenyl-, alkinyl-, and aryl-groups as well as hetero-atoms. The linker may contain up to 20 heteroatoms. The linker may also contain a reactive moiety for further modification. Preferred are linkers comprising at least one amid bond. Also preferred are linear linkers.

The term "carbocycle" comprises cyclic parts of a molecule, preferably of a linker, which may contain of from 3 to 10 carbon atoms. The "carbocycle" may also contain of from 1 to 5 non-carbon atoms. Preferred are cycloalkyles containing 5 to 7 atoms.

The term "double and triple bonds" means that said chain may contain one or more C—C double and/or C—C triple bonds.

The term "substituted by alkyl-, alkenyl-, alkinyl-groups" comprises linear, branched and cyclic groups of $C_1$ to $C_6$ with or without heteroatoms.

The term "substituted by aryl-groups" comprises carbocyclic and heterocyclic groups with 4 to 10 ring atoms.

The term "substituted by hetero-atoms" comprises the substituents —OH, =O, —O-alkyl, —O-alkenyl, —O-alkinyl, —O-aryl, —$NH_2$, —NH-alkyl, —NH-alkenyl, —NH-alkinyl, —NH-aryl, —SH, —$SO_3H$, —$S(O)_2NH_2$, —NH—$SO_2$—$CH_3$, —Cl, —I, —Br, —F.

The term "may contain up to 20 heteroatoms" means that said linear chain is optionally interrupted up to five times and/or started and/or terminated by urea or urea derivatives, thiourea, —O—, —NH—, —N($CH_3$)—, —S—, —$S(O)_2$—, —$S(O)_2O$—, —$OS(O)_2$—, —$S(O)_2NH$—, —$NHS(O)_2$—, —C(O)—, —OC(O), —C(O)O—, —NHC(O)— or —C(O)NH—. Preferably said linear chain is optionally interrupted or started or terminated by —O—, —NH—, —NHC(O)— or —C(O)NH—.

The term "reactive group" comprises a moiety capable of attaching a detectable label. The reactive group is optionally protected by appropriate protective groups which are compatible with oligonucleotide synthesis. Said reactive group is selected from the group consisting of N-succinimidyl-oxycarbonyl, maleinimido, 4,6-dichloro-[1,3,5]triazin-2-amino-, N-benzotriazolyl-oxycarbonyl, N-phthalimidyl-oxycarbonyl, carboxylic acid, alkylcarbonyl-oxycarbonyl, arylcarbonyl-oxycarbonyl, alkoxycarbonyl, aryloxycarbonyl, imidate, imidazolide, p-aminobenzoyl, —C(O)Cl, —C(O)Br, —C(O)I, —$SO_2Cl$, —$SO_2Br$, —$SO_2I$, —$NH_2$, —$N_3$, —N=C=O, —N=C=S, —$N_2^+$, —Cl, —Br, —I, —O—$NH_2$ or —N(R)—$NH_2$, whereby R is a $C_1$ to $C_6$ alkyl residue. The preferred reactive groups are N-succinimidyl-oxycarbonyl, maleinimido, carboxylic acid, alkylcarbonyl-oxycarbonyl, arylcarbonyl-oxycarbonyl, alkoxycarbonyl, aryloxycarbonyl, —$NH_2$, —$N_3$, —N=C=O, —N=C=S, —$N_2^+$, —Cl, —Br, —I, —O—$NH_2$, OH, SH, or —N($CH_3$)—$NH_2$. The —$NH_2$ group and its variants and analogs are the most preferred reactive groups and if used directly in oligonucleotide synthesis, this reactive group is protected with trifluoro acetyl. The reactive group is optionally attached via a linker.

The term "CPG" or "controlled pore glass" means available supports for the synthesis of oligonucleotides. The term CPG compromises synthesis supports which are used in standard oligonucleotide synthesis in order to attach signal entities, reactive groups, a nucleobase or analogs thereof or a phosphate to an oligonucleotide.

"Phosphoramidites" denotes molecules having a trivalent phosphorus atom which can be coupled to the 5'-terminal end of a nucleoside or nucleoside derivative. Thus phosphoramidites can be used to synthesize oligo-nucleotides. In addition to the (deoxy-)ribonucleotide phosphoramidites that are used for chain extension, there are also phosphoramidites derivatized with a label which can be used in analogous processes to label the oligonucleotide during, at the beginning, or at the end of oligonucleotide synthesis (Beaucage, Methods in Molecular Biology, ed. by S. Agrawal, vol. 20, p. 33-61 (1993); also in Wojczewski, C., et al., Synlett 10 (1999) 1667-1678). In principle synthesis could also be performed in the 5' to 3' direction. This requires a phosphoramidate group on the 5' position and a protective group on the 3' position of the phosphoramidite.

Appropriate combinations of the above defined constituents according to chemical requirements and reasonable logic can be easily assembled by a person skilled in the art.

To this day effective covalent labeling systems for oligo- and polynucleotides are only realized for the 3'- and 5'-terminal positions. In these positions dyes are incorporated during chemical oligonucleotide synthesis. For an internal labeling suitable labels, i.e. modified bases, have to be synthesized for all four nucleobases individually, e.g. TAMRA for uridine (see e.g. Walton, T. A., et al., Bioconjugate Chem. 13 (2002) 1155-1158).

With the current invention improved labeling reagents are provided. These reagents can be easily incorporated during chemical and enzymatic synthesis at any position, i.e. at the 3'-position, the 5'-position, internally as substituent and as insertion (see e.g. Verma, S., and Eckstein, F., Annu. Rev. Biochem. 67 (1998) 99-134).

The 3-substituted methanesulfonylamino indole nucleoside of the invention has the general Formula I:

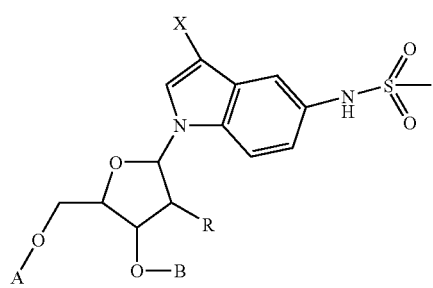

Formula I wherein A and B are independent from each other and independent from R and X, and whereby A and B are selected from the group consisting of hydrogen, a protecting group, a solid phase with a linker, a phosphoramidite, a H-phosphonate, a triphosphate, a phosphate, and a chain of nucleotide residues, with the proviso that A but not B is a triphosphate, with the proviso that if one of A or B is a phosphoramidite or a H-phosphonate, the other of A and B is a protective group and R is not OH, with the proviso that only one of A and B is a solid phase with a linker, and whereby R=H, OH, O-alkyl, O-alkenyl, O-alkinyl, O-protective group, or F, X is either a reactive group or a protected reactive group or a linker with a reactive group or a linker with a protected reactive group or a signal entity or a protected signal entity or a linker with a signal entity or a linker with a protected signal entity.

Compounds of Formula I wherein B is either a phosphoramidate group, an H-phosphonate, or a CPG and A is a protective group or vice versa are permitting two alternative synthetic routes for oligonucleotides:
- synthesis of oligonucleotides in the presence of a labeling group and
- synthesis of oligonucleotides in the presence of a reactive group for post synthesis modifications/labeling.

Compounds of Formula I, wherein B is either a phosphoramidate group, a H-phosphonate, or a CPG and A is a protective group or vice versa, i.e. A is either a phosphoramidate group, a H-phosphonate, or a CPG and B is a protective group, are used as labeling compounds in oligonucleotide synthesis, i.e. as compounds which allow during oligonucleotide synthesis the incorporation of a detectable label or a reactive group for post-synthesis labeling in the synthesized oligonucleotide.

The method of the invention for the synthesis of oligonucleotides comprises the step of incorporating a labeling compound according to the invention during oligonucleotide synthesis.

Another method of the invention for the synthesis of oligonucleotides comprises the steps of i) incorporating a labeling compound according to the invention during oligonucleotide synthesis, wherein said labeling compound contains a reactive group for coupling of a signal entity to said reactive group, and ii) coupling of a signal entity to said reactive group either during or after oligonucleotide synthesis, preferably after oligonucleotide synthesis.

With the compounds of the invention the synthesis of oligonucleotides comprising a compound of Formula I is enabled. Such an oligonucleotide comprise at least one compound of Formula I either having a reactive group or having a signal entity. In one embodiment such an oligonucleotide comprises at least two compounds of Formula I each having a signal entity, preferably such a oligonucleotide comprises one, two, three or four compounds of Formula I each having a signal entity.

Figure 1B:
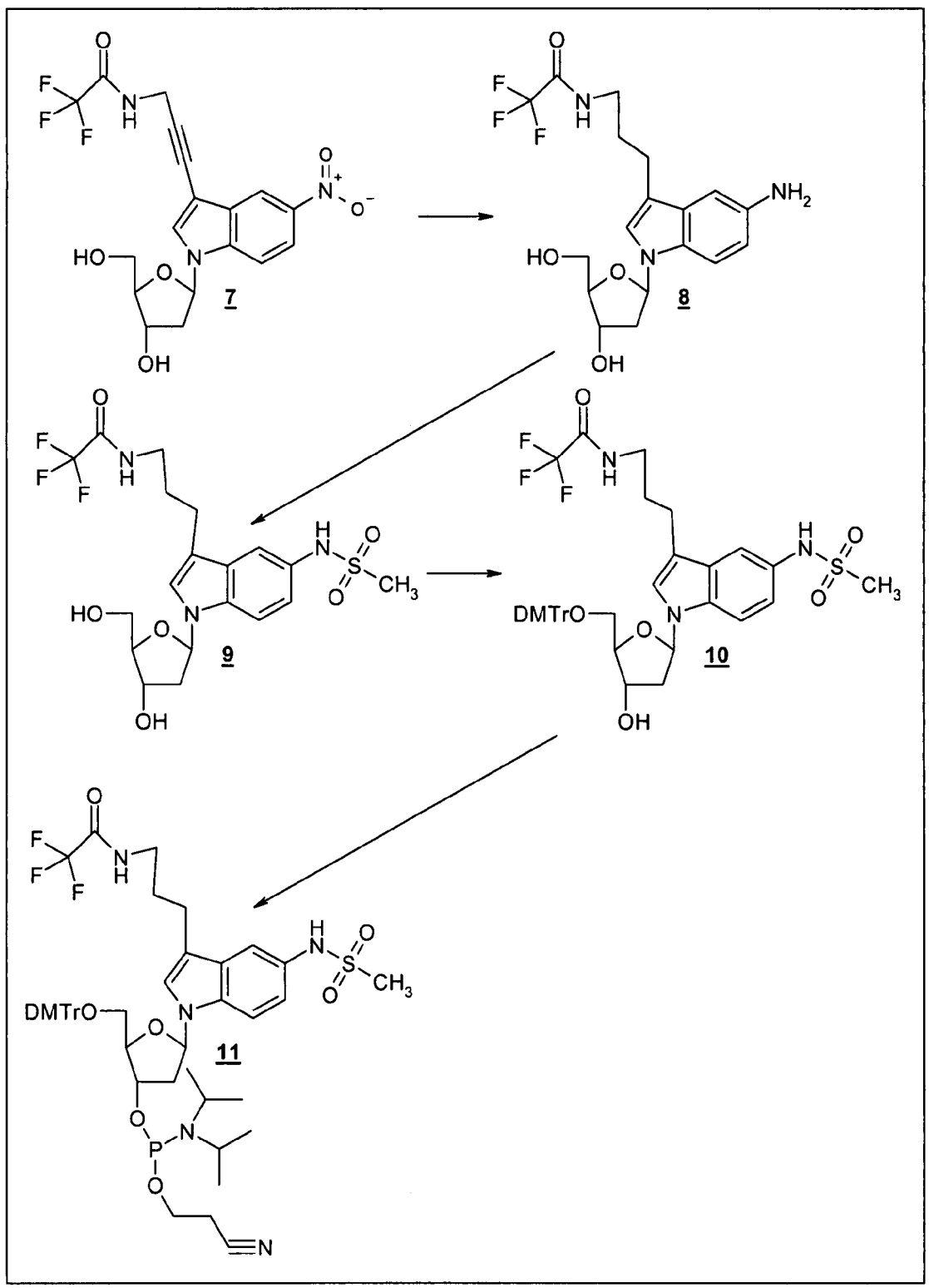
FIG. 1b: Synthetic route to a nucleoside with reactive group (7=2,2,2-Trifluoro-N-{3-[1-(4-hydroxy-5-hydroxymethyl-tetrahydro-furan-2-yl)-5-nitro-1H-indol-3-yl]-prop-2-ynyl}-acetamide; 8=N-{3-[5-Amino-1-(4-hydroxy-5-hydroxymethyl-tetrahydro-furan-2-yl)-1H-indol-3-yl]-propyl}-2,2,2-trifluoro-acetamide; 9=2,2,2-Trifluoro-N-{3-[1-(4-hydroxy-5-hydroxymethyl-tetrahydro-furan-2-yl)-5-methanesulfonylamino-1H-indol-3-yl]-propyl}-acetamide; 10=N-[3-(1-{5-[Bis-(4-methoxy-phenyl)-phenyl-methoxymethoxymethyl]-4-hydroxy-tetrahydro-furan-2-yl}-5-methanesulfonylamino-1H-indol-3-yl)-propyl]-2,2,2-trifluoro-acetamide, DMTr=Bis-(4-methoxy-phenyl)-phenyl-; 11=Diisopropyl-phosphoramidous acid 2-[bis-(4-methoxy-phenyl)-phenyl-methoxymethyl]-5-{5-methanesulfonylamino-3-[3 -(2,2,2-trifluoro-acetylamino)-propyl]-indol-1-yl}-tetrahydro-furan-3-yl ester 2-cyano-ethyl)
Figure 1C:
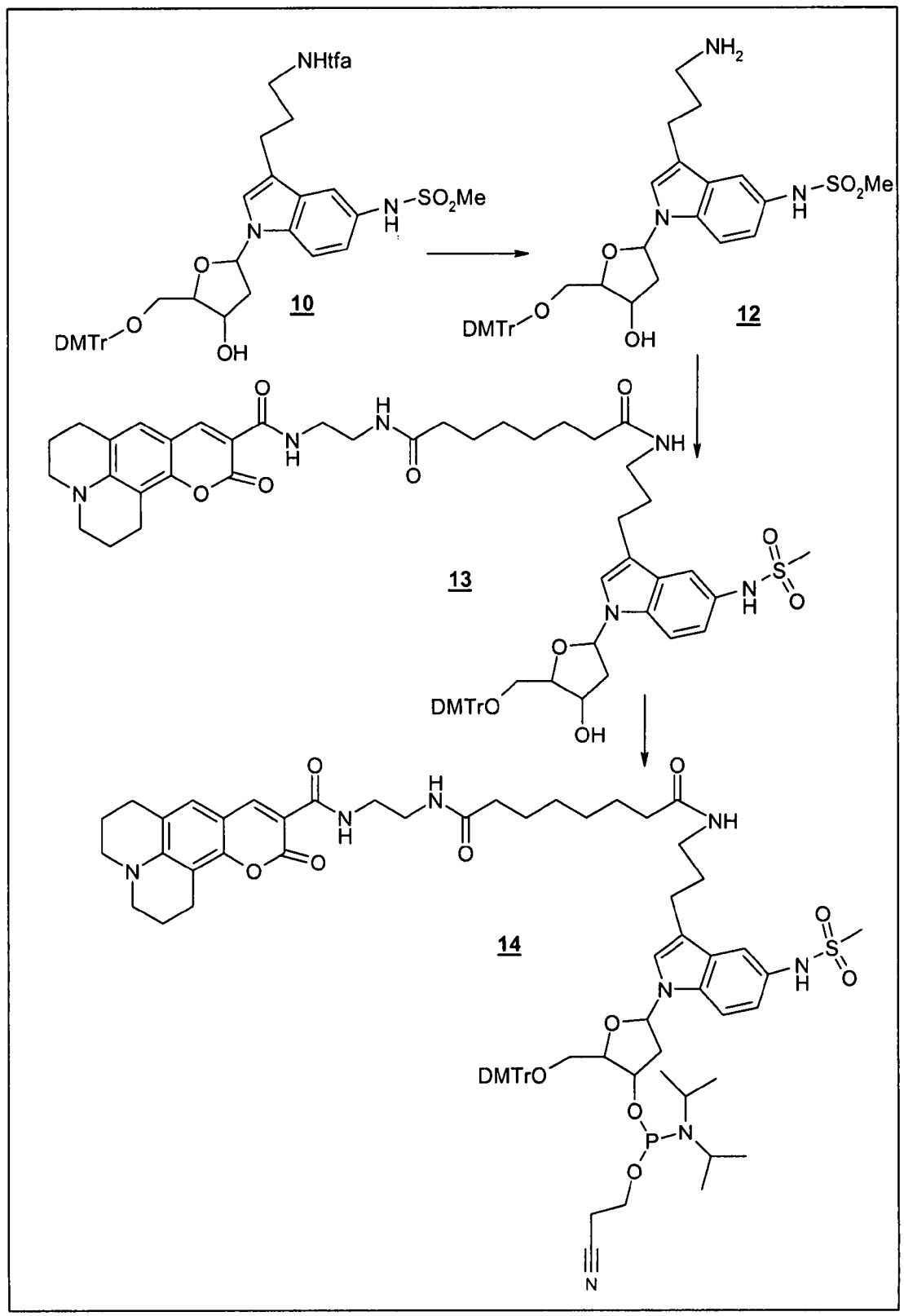
FIG. 1c: Synthesis of a Coumarin phosphoramidite (10=N-[3-(1-{5-[Bis-(4-methoxy-phenyl)-phenyl-methoxymethoxymethyl]-4-hydroxy-tetrahydro-furan-2-yl}-5-methanesulfonylamino-1H-indol-3-yl)-propyl]-2,2,2-trifluoro-acetamide, DMTr=Bis-(4-methoxy-phenyl)-phenyl-; 12=5-[3-(3-amino-propyl)-5-methylamino-indol-1-yl]-2-methoxymethyl-tetrahydro-furan-3 -ol); 13=Octanedioic acid {3-[1-(4-hydroxy-5-hydroxymethyl-tetrahydro-furan-2-yl)-5-methanesulfonylamino-1H-indol-3-yl]-propyl}-amide {2-[(10-oxo-2,3,5,6-tetrahydro-1H,4H,10H-11-oxa-3a-aza-benzo[de]anthracene-9-carbonyl)-amino]-ethyl}-amide; 14=labeled phosphoramidite)

The compounds of Formula I are accessible via chemical synthesis. An exemplary synthetic procedure for a compound of Formula I with A=dimethoxy trityl (DMTr), B=a phosphoramidite group, X=reactive group with linker is outline in FIGS. 1a, 1b and 1c as well as in Example 1.

The starting point of the synthesis is 5-nitroindole which in the first step is substituted in the 3-position with iodine. Following the introduction of the iodine substituent in the 3-position is the assembly of the nucleoside basic structure by introducing a protected deoxypentose at the N-atom of the nitroindole. After deprotection of the hydroxyl groups a linker moiety bearing a protected reactive group is introduced. This linker moiety comprises mainly carbon, oxygen and nitrogen atoms. The role of the linker is on the one hand to provide a reactive group for the introduction of the detectable label and on the other hand to provide a flexible spacer allowing the detectable label to orient properly.

At this point the two synthetic routes diverge. If a label, that does not tolerate the conditions during oligonucleotide synthesis, shall be attached, the phosphoramidite residue is introduced at this stage. With this unlabelled nucleotide phosphoramidite bearing a protected reactive group the oligonucleotide synthesis is carried out and after synthesis and deprotection the detectable label is introduced in the final oligonucleotide.

If a label, that tolerates the conditions during oligonucleotide synthesis, shall be used the label is introduced prior to the formation of the amidite.

The phosphor-amidite chemistry method is well known by any person skilled in the art. A 3'-phosphorous group of one nucleotide reacts with the 5'-hydroxyl moiety of another. The reaction proceeds from the 3'- to 5'-end, between each phosphor-amidite with a 5'-dimethoxytrityl protected monomer delivered in solution and the growing, 3' reactive oligonucleotide bound to an inert substrate.

Nascent oligonucleotides have the 5'-hydroxyl positions protected by dimethoxytrityl (DMTr) groups, which have to be removed after each synthesis cycle in order to generate a reactive 5'-OH group of the nascent oligonucleotide chain. For product oligonucleotides, the DMTr group can be removed during synthesis (TRITYL OFF) or left on (TRITYL ON), if reverse phase HPLC is the purification method of choice.

An example for the synthesis of a phosphoramidite bearing a reactive group is given in example 1a, the synthesis of a labeled phosphoramidite is described in example 1c. Other phosphoramidites bearing a reactive group or a label can be synthesized correspondingly.

The phosphoramidites according to the invention can be used during oligonucleotide synthesis for providing oligonucleotides, which are bearing a label or a reactive group, at any position of the oligonucleotide.

The oligonucleotide may comprise a mixture of different modified nucleotides and different labels. For example, the synthesized oligonucleotide may comprise either one, two, or more compounds according to the invention with or without a label. In an alternative embodiment, the oligonucleotide may comprise one or more compounds according to the invention and at the same time one or more other compounds, all having a detectable label, either the same or a different. The combination of the different labels and compounds is depending of the application for which the oligonucleotide is synthesized.

The synthesis of oligonucleotides is based on the method developed by Caruthers in the early eighties (Beaucage, S. L., and Caruthers, M. H., Tetrahed. Lett. 22 (1981) 1859-1862; McBride, L. J., and Caruthers, M. H., Tetrahed. Lett. 24 (1983) 245-248; for further reference see: Oligonucleotide Synthesis: A Practical Approach, Gait, ed., IRL Press, Oxford (1984); Kuijpers, W. H. A., et al., Nucleic Acids Research 18 (1990) 5197-5205; Dueholm, K. L., J. Org. Chem. 59 (1994) 5767-5773, Agrawal, S. (ed.) Methods in Molecular Biology, volume 20). In the first step the DMTr protecting group is removed with a slightly acidic solution of, e.g., dichloroacetic acid or trichloroacetic acid in dichloromethane. For coupling the nucleoside which is to be coupled to the deprotected hydroxyl group is activated with tetrazole. The reaction product is afterwards oxidized, e.g. with an iodine/water/base mixture. The cycle is completed by capping hydroxyl groups that were not coupled during the coupling reaction.

An example for the synthesis of an oligonucleotide is given in Example 2.

The oligonucleotides synthesized with the labeled base according to the current invention incorporated at any position in the oligonucleotide are useful for many PCR applications. These pave the way for improved and new applications in nucleic acid chemistry.

In one embodiment, oligonucleotides containing an internal label according to the invention are used as hybridization probes. The internal label may be an integral part of any kind of hybridization probes such as Taqman probes, Molecular Beacons or may be an integral part of one or both members of a pair of FRET hybridization probes. Those hybridization probes according to the invention may be used for hybridization on blots, microtiter plates, microarrays, and, in particular, for real time PCR.

In one embodiment of the current invention the labeled nucleotide is used in a hybridization probe as a member of one pair of FRET hybridization probes. This use is not limited to a single pair but can be expanded to the application in a FRET multiplex hybridization assay.

In one embodiment the hybridization probe containing one or more labeled nucleotides according to the invention is employed as a Taqman probe or a Molecular Beacon probe.

In one embodiment two compounds of Formula I, bearing signal entities, are present in an oligonucleotide, preferably the signal entities are fluorescent dyes.

In the three above mentioned hybridization probe formats the interaction of at least two signal entities is required. These pairs are preferably a fluorescent dye and a quencher or two fluorescent dyes.

In an embodiment of the invention, using a pair of FRET hybridization probes according to the invention, temperature dependence of hybridization is monitored, for example by means of performing a melting curve analysis. In an alternative embodiment, a hybridization probe according to the invention is used for monitoring the temperature dependence of hybridization.

Real time PCR melting curve analysis is usually performed after completion of the PCR-reaction. After an initial denaturation and cooling step, the temperature of the amplicon is continuously increased, and fluorescence is detectable as long as the hybridization probe is bound to the target DNA. In case of the FRET hybridization probe format, both probes need to stay hybridized to the target nucleic acid in order to generate a fluorescent signal. At the melting temperature, the hybridization probes (in case of the FRET format: at least one member of said pair of hybridization probes) are released from their target, and the fluorescent signal is decreasing immediately down to the background level.

This decrease is monitored with an appropriate fluorescence versus temperature-time plot such that a first derivative value can be determined, and accordingly determined at which temperature the maximum of fluorescence decrease is observed.

One aspect of the present invention is based on the usage of differently labeled hybridization reagents, each reagent comprising a pair of FRET hybridization probes, comprising a pair of two fluorescent dyes which interact with each other on the principle of fluorescence resonance energy transfer (FRET).

More precisely, such a hybridization reagent is composed of two adjacently hybridizing oligonucleotides, appropriately labeled such that together they can act according to the FRET-hybprobe detection format as reported in WO 97/46707, WO 97/46712, and WO 97/46714.

In case of the FRET hybprobe format a pair of oligonucleotides acts together as a donor probe and an acceptor probe. Yet, in other cases there may exist many other sequence variants in the target sequences which need to be detected. Thus it may be impossible to detect the sequences of all members by just using one pair of FRET oligonucleotide hybridization probes.

An important and significant method for the detection and mapping of e.g. single nucleotide polymorphisms (SNPs), i.e. the variation of a single base in a polynucleotide sequence, is the melting curve analysis. By heating double stranded polynucleotide molecules the hydrogen bond based interactions holding the strands together are reduced. At a specific temperature the two stands dissociate. This temperature is dependent on the length of the double stranded polynucleotide, the degree of GC content and the degree of complementarity between the stands. The temperature at which 50% of the double stranded polynucleotide becomes single stranded is termed melting temperature $T_m$.

This technique is especially important for the analysis of heteroduplexes formed between single stranded polynucleotide molecules and sequence-specific oligonucleotide probes. As already mentioned above the melting temperature is depending on the complementarity of the two singles strands. This parameter is very sensitive so that actually one single base mismatch is detectable by a decrease of the melting temperature. That means, probe/polynucleotide heteroduplexes containing only a single mismatch are melting at a lower temperature than perfectly paired heteroduplexes. This demonstrates that even very small destabilization effects can be detected and quantified.

A melting curve analysis comprises in general three steps. In the first step a sequence-specific fluorescence labeled oligonucleotide probes is added to the PCR mixture. The second step comprises the amplification of the polynucleotide by PCR, and in the third step the formed heteroduplexes between the single stranded target polynucleotide and the probes are slowly heated, and the changes in fluorescence are recorded in dependency to the temperature which results in the recording of a melting curve.

The signal enhancement is also important for real time PCR applications. In these applications the fluorescence signal emitted from heteroduplexes of amplified polynucleotide and labeled probe oligonucleotide is used for relative and absolute quantitation of the polynucleotide number and concentration. Among others determination of viral loadings or diagnosis of tumors as well as determination of gene expression are application areas of quantitative real-time PCR.

In hydrolysis probe formats, e.g. TaqMan, the signal increases during hydrolysis since the coumarin is cleaved during the PCR by the Taq polymerase. As could be seen from FIG. 2 the linker has an influence on signal increase, i.e. the signal increase increases with the length of the linker, and therefore the fluorescence properties could be adapted to different applications. For Hydrolysis probe format its desirable to have a highly fluorescent reporter whereas for multiplexing with the Hybprobe format it could be of advantage if the FRET donor signal is weak.

The following examples, references, sequence listing and figures are provided to aid the understanding of the present invention, the true scope of which is set forth in the appended claims. It is understood that modifications can be made in the procedures set forth without departing from the spirit of the invention.

Specific Embodiments

Brief Description of the Sequences and Examples

SEQ ID NO: 01: Terminally labeled probe
SEQ ID NO: 02: Dual labeled probe
SEQ ID NO: 03: Forward primer of Example 3
SEQ ID NO: 04: Reverse primer of Example 3
Example 1a: Synthesis of a phosphoramidite for oligonucleotide synthesis bearing a reactive group
Example 1b: Synthesis of a reactive label
Example 1c: Synthesis of a labeled phosphoramidite for oligonucleotide synthesis
Example 2: Oligonucleotide synthesis
Example 3: Detection of viral target DNA by RT-PCR Unless otherwise stated, all chemicals were reagent grade and were purchased from Sigma-Aldrich. The chemicals were used as received from the manufacturer or supplier.

EXAMPLE 1a

Preparation of Indole Nucleoside

3-Iodo-5-nitro-indole

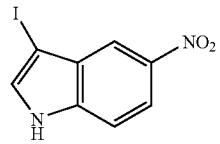

25.0 g (154.2 mmol) 5-nitroindole (Aldrich N1, 760-2) and 21.7 g (386.7 mmol) potassium hydroxide were dissolved in 270 ml DMF. To this solution 39.5 g (155.6 mmol) iodine dissolved in 250 ml DMF were added drop wise during one hour. The resulting mixture was subsequently stirred for 1.0 h at room temperature. Afterwards the reaction mixture was poured on 2.5 l of sludge. The formed precipitate was collected by filtration and washed twice with water. The residue obtained was dried in a vacuum (yield: 43.0 g).

5-chloro-2-(4-methyl-benzoyloxymethyl)-3-(4-methyl-benzoyloxy)-tetrahydro-furan

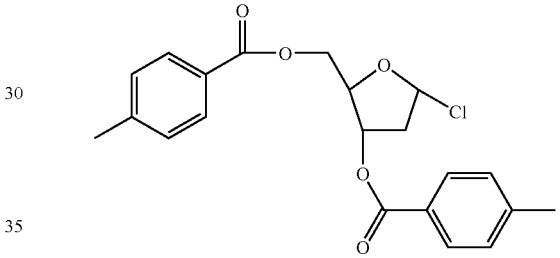

45.0 g (335.5 mmol) of 2-deoxy-D-ribose (Fluka 31170) were dissolved in 540 ml of anhydrous methanol. To this solution a mixture of 90 ml methanol and 1.53 ml (21.5 mmol) acetyl chloride (Aldrich 40,279-6) were added drop wise at room temperature. The resulting mixture was stirred for an additional 15 min. at room temperature. After the addition of 18.0 g (214.3 mmol) sodium bicarbonate the resulting suspension was stirred for 15 min. After filtration of the suspension the solvent was removed by distillation. To the oily brown residue 75 ml of anhydrous pyridine were added and subsequently the solvent was removed in a vacuum on a rotary evaporator. This procedure was repeated three times. The remaining residue was dissolved in 270 ml anhydrous pyridine and cooled to 0° C. At this temperature 99 ml (748.6 mmol) of p-toluoyl chloride (Aldrich 10,663-1) were added drop wise over a period of 90 minutes. Afterwards the reaction mixture was stirred for an additional 12 hours at room temperature. The suspension was poured on 1.5 l sludge and the aqueous phase was extracted three times each with 600 ml dichloromethane. The combined organic phases were washed twice each with 600 ml water, three times each with 600 ml 2 M hydrochloride acid, twice each with 600 ml saturated sodium bicarbonate solution and twice each with 600 ml water. Afterwards the separated organic phase was dried over sodium sulfate and evaporated to dryness in a vacuum on a rotary evaporator. The oily residue was dissolved in 180 ml glacial acetic acid and 280 ml of a mixture of 228 ml glacial acetic acid, 45.9 ml (646 mmol) acetyl chloride and 11.3 ml water were added with stirring and with cooling on ice. The pulp was removed by filtration and washed twice each with 200 ml of ice cold diethyl ether. The residue was dried over potassium hydroxide in a vacuum. (yield: 96.3 g).

5-(3-Iodo-5-nitro-indol-1-yl)-2-(4-methyl-benzoyloxymethyl)-3-(4-methyl-benzoyloxy)-tetrahydro-furan

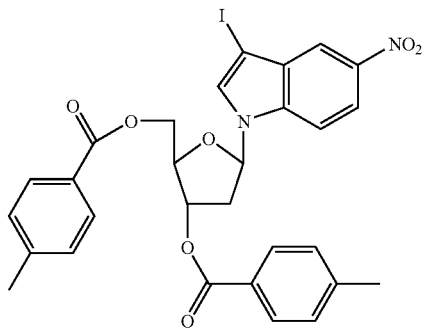

To a suspension of 1.0 g (3.5 mmol) 3-iodo-5-nitroindole in 15 ml acetonitrile were added 0.16 g (6.7 mmol) sodium hydride (Aldrich 223441-50G). The stirring was continued and the suspension turned red. After 15 min. 2.02 g (5.2 mmol) 5-chloro-2-(4-methyl-benzoyloxymethyl)-3-(4-methyl-benzoyloxy)-tetrahydro-furan were added in small portions and the stirring was continued for another 60 minutes at room temperature. The precipitate was removed by filtration and washed once with acetonitrile. The combined yellow filtrates were concentrated until a product precipitated. For complete precipitation of the product 50 ml ethanol were added. The yellow precipitate was removed by filtration und washed with ethanol. The residuum was dried over phosphorus pentoxide and potassium hydroxide in a vacuum (yield: 1.9 g).

2-Hydroxymethyl-5-(3-iodo-5-nitro-indol-1-yl)-tetrahydro-furan-3-ol

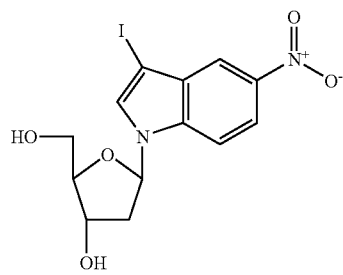

To a suspension of 12 g (18.7 mmol) of the indole derivative 5-(3-Iodo-5-nitro-indol-1-yl)-2-(4-methyl-benzoyloxymethyl)-3-(4-methyl-benzoyloxy)-tetrahydro-furan in 600 ml ethanol 4.2 g (37.5 mmol) potassium tert-butylate were added. The suspension was stirred for 12 hours at room temperature. The resulting yellow solution was chromatographed on a silica gel column (Silica gel 60, Merck, 230×100 mm) with a gradient starting at 100% dichloromethane to 85% dichloromethane: 15% methanol (yield: 6.6 g).

2,2,2-Trifluoro-N-prop-2-ynyl-acetamide

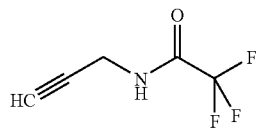

To 15 g (272.3 mmol) propargylamine in 275 ml anhydrous methanol 36.6 g (285.9 mmol) methyl trifluoroacetate were added with cooling. The resulting reaction mixture was stirred for an additional four hours at room temperature. Afterwards the solvent was removed by distillation at reduced pressure. The residue was dissolved in 300 ml trichloromethane and extracted four times, twice each with 300 ml of a saturated sodium bicarbonate solution and twice each with 300 ml water. The separated organic phase was dried over magnesium sulfate, filtrated and the solvent was removed by distillation (yield: 23.3 g).

2,2,2-Trifluoro-N-{3-[1-(4-hydroxy-5-hydroxymethyl-tetrahydro-furan-2-yl)-5-nitro-1H-indol-3-yl]-prop-2-ynyl}-acetamide

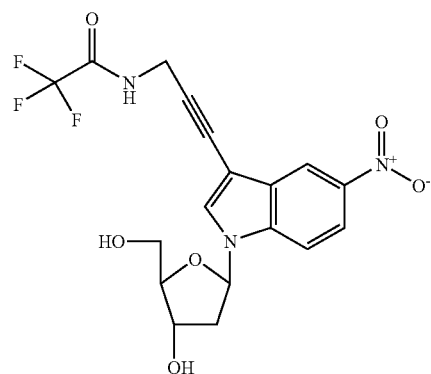

19.8 g (48.99 mmol) of 2-hydroxymethyl-5-(3-iodo-5-nitro-indol-1-yl)-tetrahydro-furan-3-ol were placed in a preheated flask in an argon atmosphere and dissolved in 200 ml anhydrous tetrahydrofuran. 27.2 ml (196.2 mmol) of triethylamine (Merck, 8.08352.1000), 1.87 g (9.82 mmol) of copper (I) iodide (Merck, 8.18311.0100) and 5.66 g (4.89 mmol) of tetrakis(triphenylphosphine)palladium(0) (Merck, 8.14761.005) were added. After 5 minutes at room temperature 19.8 ml of 2,2,2-trifluor-N-propyl-2-ynyl-acetamide were added and it was stirred for a further 45 minutes. The solvent was removed by distillation. The residue was chromatographed on a silica gel column (Silica gel 60, Merck, 400×70 mm) with a gradient starting at 100% dichloromethane to 95% dichloromethane with 5% methanol (yield: 17.06 g).

N-{3-[5-Amino-1-(4-hydroxy-5-hydroxymethyl-tetrahydro-furan-2-yl)-1H-indol-3-yl]-propyl}-2,2,2-trifluoro-acetamide

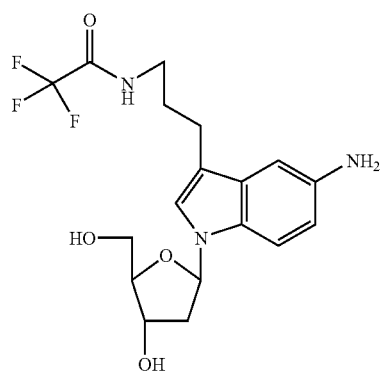

4.0 g (9.3 mmol) 2,2,2-Trifluoro-N-{3-[1-(4-hydroxy-5-hydroxymethyl-tetrahydro-furan-2-yl)-5-nitro-1H-indol-3- yl]-prop-2-ynyl}-acetamide and 650 mg 5% (w/w) palladium on charcoal (Fluka No: 75992) were suspended in 100 ml anhydrous ethanol and placed under argon atmosphere in a flask. The argon was substituted by hydrogen (Whatman hydrogen generator). The hydrogenation was monitored by TLC (Silica Gel Merck F60, developing solvent: toluene/acetic acid ethyl ester/methanol 4:1:1 (v/v/v)) and stopped when the starting material was no longer detectable. The catalyst was removed by filtration and the solvent evaporated to dryness in a vacuum on a rotary evaporator. The product was used without further purification (yield: 3.7 g).

2,2,2-Trifluoro-N-{3-[1-(4-hydroxy-5-hydroxymethyl-tetrahydro-furan-2-yl)-5-methanesulfonyla-1H-indol-3-yl]-propyl}-acetamide

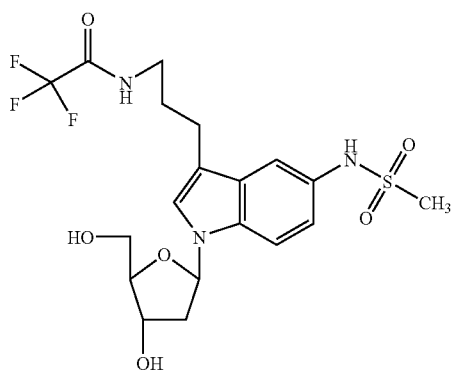

3.7 g (9.2 mmol) N-{3-[5-Amino-1-(4-hydroxy-5-hydroxymethyl-tetrahydro-furan-2-yl)-1H-indol-3-yl]-propyl}-2,2,2-trifluoro-acetamide was dissolved in 30 ml anhydrous pyridine. 0.72 ml (9.2 mmol) methylsulfonylchloride were added. The reaction was monitored by TLC (Silica Gel Merck F60, toluene/acetic acid ethyl ester/methanol 3:2:1 (v/v/v)). After 20 minutes with stirring the solvent was removed by in a vacuum on a rotary evaporator. The residue was dissolved in ethyl acetate and washed three times with each 100 ml of 10% (w/v) aqueous solution of citric acid and afterwards once with 100 ml brine (saturated sodium chloride solution). The organic phase was separated and dried over sodium sulfate. For further purification the residue was chromatographed on a silica gel column (Silica gel 60, Merck, 185×85 mm) with toluene/acetic acid ethyl ester/methanol 3:2:1 (v/v/v) as mobile phase. The fractions containing the product were combined and the solvent was removed in a vacuum on a rotary evaporator (yield: 720 mg).

N-[3-(1-{5-[Bis-(4-methoxy-pheny)-phenyl-methoxymethoxymethyl]-4-hydroxy-tetrahydro-furan-2-yl}-5-methanesulfonylamino-1H-indol-3-yl)-propyl]-2,2,2-trifluoro-acetamide

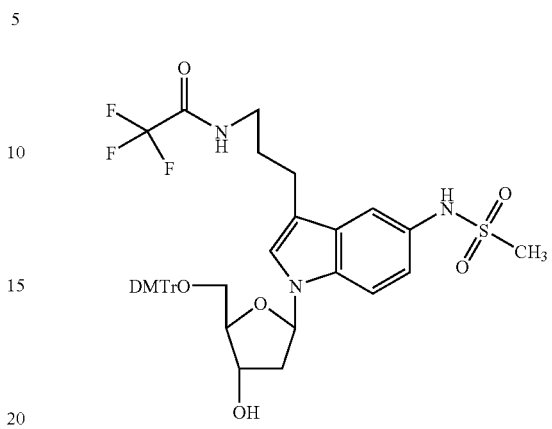

0.7 g (1.45 mmol) 2,2,2-Trifluoro-N-{3-[1-(4-hydroxy-5-hydroxymethyl-tetrahydro-furan-2-yl)-5-methanesulfonylamino-1H-indol-3-yl]-propyl}-acetamide and 540 mg (1.5 mmol) of 4,4'-dimethoxytriphenylmethyl chloride (Aldrich No: 10,001-3) were placed in a flame dried 50 ml flask under an argon atmosphere. The substances were dissolved in 15 ml anhydrous pyridine and stirred for three hours with exclusion of humidity. 0.5 ml methanol were added and the solvent was removed in a vacuum on a rotary evaporator. The residue was chromatographed on a silica gel column (Silica gel 60, Merck, 280×50 mm) with toluene/ethyl acetate/methanol 4:1:1 (v/v/v) supplemented with 0.1% (v/v) triethylamine. The fractions were monitored by TLC (silica gel, toluene/ethyl acetate/methanol 4:1:1 (v/v/v)). The desired fractions were combined and the solvents were removed in a vacuum on a rotary evaporator with a water bath temperature of 38° C. (yield: 660 mg).

Diisopropyl-phosphoramidous acid 2-[bis-(4-methoxy-phenyl)-phenyl-methoxymethyl]-5-{5-methanesulfonylamino-3 -[3-(2,2,2-trifluoro-acetylamino)-propyl]-indol-1-yl}-tetrahydro-furan-3-yl ester 2-cyano-ethyl

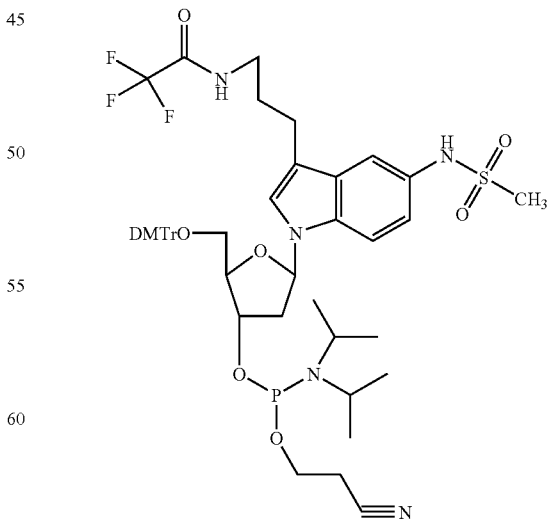

610 mg (0.77 mmol) N-[3-(1-{5-[Bis-(4-methoxy-phenyl)-phenyl-methoxymethoxymethyl]-4-hydroxy-tetrahydro-furan-2-yl}-5-methanesulfonylamino-1H-indol-3 -yl)-propyl]-2,2,2-trifluoro-acetamide, 0.44 ml (2.55 mmol) N-ethyl-diisopropyl amine (Fluka No: 03440) and 0.19 ml (0.85 mmol) chloro-2-cyanoethoxydiisopropylamino-phosphan-monochloride were sequentially dissolved in 15 ml anhydrous dichloromethane in a dried reaction flask under an argon atmosphere. The sealed reaction vessel was stirred for 50 minutes. The reaction was stopped with the addition of 0.1 ml methanol and than the mixture was directly chromatographed on a silica gel column (silica gel 60, Merck, 120×30 mm) with a gradient from dichloromethane with 0.1% (v/v) triethylamine to dichloromethane:acetone 95:5 (v/v) with 0.1% (v/v) triethylamine. The product containing fractions were combined and the solvent was removed in a vacuum on a rotary evaporator (bath temperature 28-30° C.). The resulting oil was dissolved in 15 ml dichloromethane and the solvent was evaporated. The remaining residue was dissolved in 20 ml dichloromethane and apportioned to a glass bottle compatible with an ABI DNA synthesizer. The solvent was removed in a stream of nitrogen (yield: 410 mg).

NMR, solvent: $d_6$-DMSO, model: BrukerDPX-300, 300 MHz, $^{31}$P-NMR: 148.79 (d), 1H: 9.45(t) [1H], 9.33(s) [1H], 7.58(d) [1H], 7.17-7.56 (m) [11H], 7.02 (d)[1H], 6.80 (m) [4H] 6.36 (dd) [1H], 4.75 (m) [1H], 4.05 (d)[1H], 3.54-3.73 (m)[5H], 3.71(s) [6H], 3.16 (s,br) [4H] 2.86(s) [3H], 2.49-2.79 (m,s,DMSO), 1.74 (m) [2H], 1.15 -0.99 (m) [12 H]

EXAMPLE 1b

Synthesis of Reactive Label—Synthesis of Coumarin 343-aminohexanoic Acid-NHS Ester Coumarin 343-aminohexanoic Acid

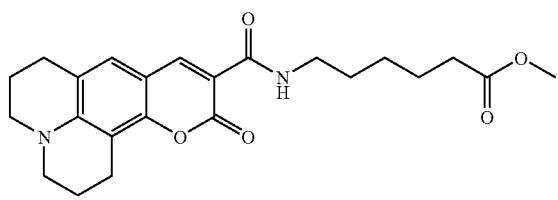

Coumarin 343 (5 mmol, Aldrich No. 393029) and each 5.5 mmol of 4-aminohexanoic acid methyl ester and HBTU (O-Benzotriazole-N,N,N',N'-tetramethyl-uronium-hexafluoro-phosphate) as well as 11 mmol triethylamine were dissolved in 100 ml DMF and stirred for 1.5 h at room temperature. The solvent is removed by evaporation on a rotary evaporator and the residuum is dissolved in trichloromethane. Residual HBTU is removed by extraction with water with 0.5 mol/l hydrochloric acid. The organic solvent is separated and evaporated to dryness in a rotary evaporator. The crude product (2.37 g) is purified by flash chromatography (silica gel 60, Merck, No: 11452134001) with a mobile phase consisting of trichloromethane:ethyl acetate 2:1 (v/v) (yield: 1.03 g).

Coumarin 343-aminohexanoic Acid

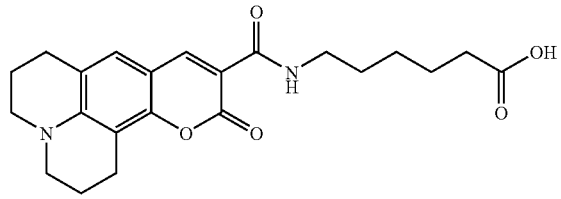

Coumarin 343-aminohexanoic acid-methyl ester (0.1 mmol) was dissolved in 200 ml phosphate buffer (10 mM, pH 7.0) and 20 mg esterase was added (EC 3.1.1.1.; Sigma No: E-3019). After stirring for three days at ambient conditions (room temperature) the methyl ester has been cleaved quantitatively. The product was isolated by extraction of the aqueous phase with trichloromethane. The separated organic phase was washed with $H_2O$ and brine ($H_2O$ saturated with NaCl). After drying over magnesium sulfate and removal of the solvent in a vacuum on a rotary evaporator, the residuum is dissolved in dioxane and lyophilized.

Coumarin 343-aminohexanoic Acid-NHS Ester

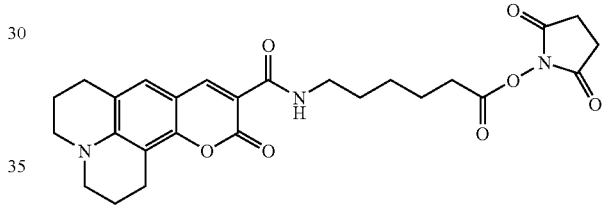

0.1 mmol Coumarin 343-aminohexanoic acid was dissolved in 20 ml DMF and a 20% molar surplus of N-hydroxysuccinimide and morpholinoethylisocyanide were added (0.12 mmol). The NHS-ester formed directly and quantitatively. Isolation was achieved by the addition of trichloromethane and washing of the organic phase twice with 50 ml of saturated NaHCO3 solution and once with NaCl saturated H2O. The solvent of the combined phases was removed in a vacuum on a rotary evaporator and the residue was lyophilized after dissolution in dioxane.

Synthesis of Reactive Label—Synthesis of Coumarin 343-aminopropionic Acid-NHS Ester Coumarin 343-aminopropionic Acid-tert-butyl Ester

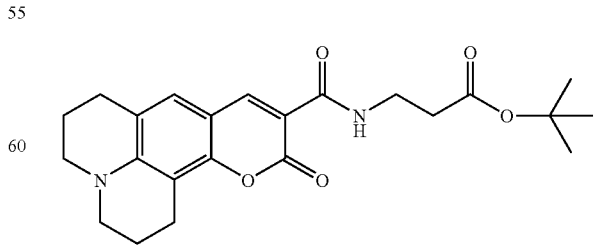

285 mg Coumarin 343 (1 mmol), 262 mg aminopropionic acid tert. butyl ester (1.2 mmol) and 343 mg HBTU (1.2 mmol) were dissolved in 5 ml of dry DMF. 280 μl triethylamine were added and the solution was stirred for 2 hours at room temperature. The solvent was evaporated in a vacuum on a rotary evaporator and the product was purified by column chromatography (silica gel 60, Merck, mobile phase: ethyl acetate/methanol 2:1 (v/v)).

Coumarin 343-aminopropionic Acid

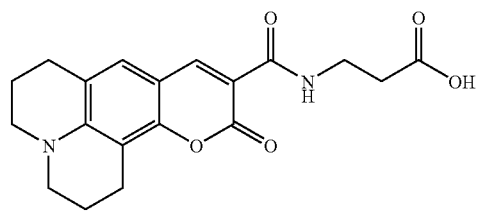

The chromatographed product of step a) was dissolved in 20 ml trifluoroacetic acid and stirred for 15 minutes at room temperature. Afterwards the liquid components were evaporated in a vacuum on a rotary evaporator. Acetone was added and the pure product is obtained as precipitate (yield: 138 mg (2 steps)).

Coumarin 343-aminopropionic Acid-NHS Ester

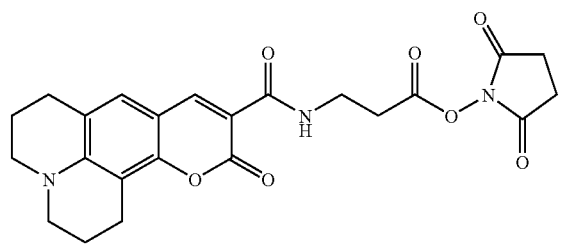

58.8 mg (0.165 mmol) Coumarin 343-aminopropionic acid were dissolved in 50 ml trichloromethane. Afterwards 0.165 mmol morpholinoethylisocyanide and 0.165 mmol N-hydroxysuccinimide were added. The solution was stirred for two hours at room temperature and thereafter 150 ml trichloromethane were added. The organic phase was washed consecutively with 80 ml 5% (w/v) NaHCO$_3$ solution, 80 ml 1 M HCl and 80 ml H$_2$0. After drying the organic phase with Na$_2$SO$_4$ the solvent was removed in a vacuum on a rotary evaporator (yield: 35 mg).

Synthesis of Label—Coumarin 343-EDA-DSS

For the synthesis of Coumarin 343-EDA-DSS 1 mmol of the starting material Coumarin 343-EDA (see e.g. Webb, R., and Corrie, J. E. T., Biophysical Journal 81 (2001) 1562-1569) is dissolved in 5 ml of dry DMF and added slowly to a DMF solution of 4 mmol DSS (disuccinimido suberate) and 2 mmol triethylamine in 10 ml of dry DMF. The mixture is stirred for 1 h at room temperature and afterwards the solvent is removed in a vacuum. The product is purified by column chromatography (silica gel, eluent: trichloromethane:acetic acid ethyl ester 1:1 (v/v) with 1% (v/v) acetic acid). (Yield: 230 mg).

EXAMPLE 1c

Synthesis of a Labeled Phosphoramidite for Oligonucleotide Synthesis

N-(3-(3-Amino-propyl)-1-{5-[bis-(4-methoxy-phenyl)-phenyl-ethoxymethyl]-4-hydroxy-tetrahydro-furan-2-yl}-1H-indol-5-yl)-methanesulfonamide

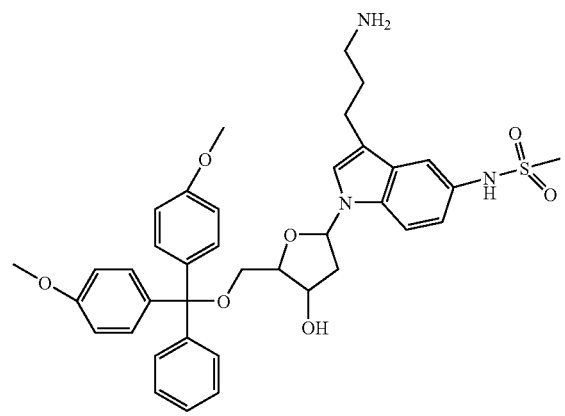

490 mg (0.64 mmol) N-[3-(1-{5-[Bis-(4-methoxy-phenyl)-phenyl-methoxymethoxymethyl]-4-hydroxy-tetrahydro-furan-2-yl}-5 -methanesulfonylamino-1H-indol-3-yl)-propyl]-2,2,2-trifluoro-acetamide were dissolved in 20 ml of a 7N ammonia solution in methanol. The solvent was removed in vacuum on a rotary evaporator. The residue (420 mg) was used without further purification.

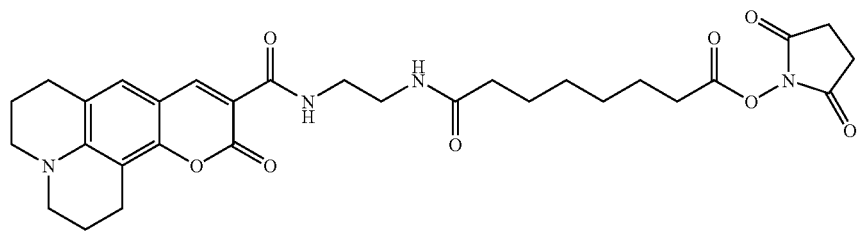

Coupling of Coumarin Dye to Indole Base

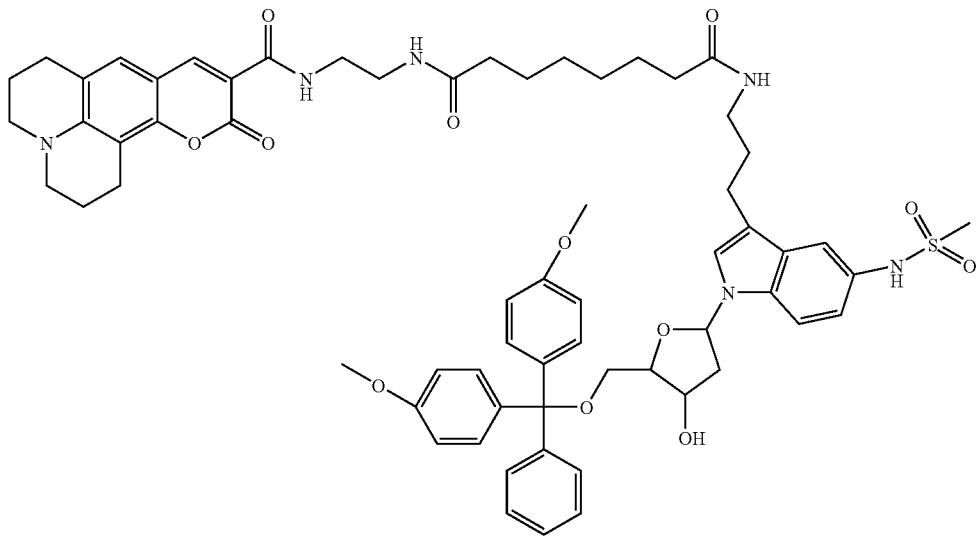

350 mg NHS ester Coumarin 343-EDA-DSS from example 1b, part III (0.60 mmol) and 0.67 ml (5 mmol) triethylamine were added to a solution of 420 mg (0.61 mmol) N-(3-(3-Amino-propyl)-1-{5-[bis-(4-methoxy-phenyl)-phenyl-ethoxymethyl]-4-hydroxy-tetrahydro-furan-2-yl}-1H-indol-5-yl)-methanesulfonamide in 20 ml dichloromethane. After stirring for 15 h at room temperature the solvent was removed in a vacuum on a rotary evaporator. The product was purified by column chromatography (silica gel 60, Merck, mobile phase: toluene:ethyl acetate:methanol 4:5:1 (v/v/v) containing 0.2% (v/v) triethylamine) (yield: 290 mg).

Synthesis of a Coumarin Sulfomethylamino Indole Phosphoramidite

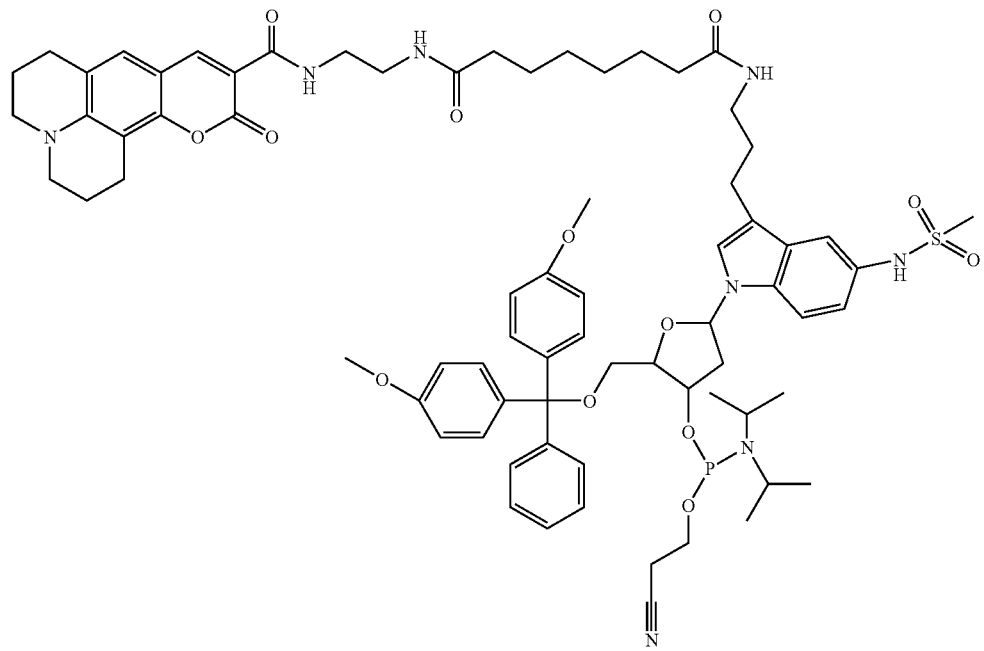

Under an argon atmosphere 65.8 mg (62 µl, 0.27 m mmol) of chlor-2-cyanoethoxy diisopropyl aminophosphane were added with stirring to a mixture of 290 mg (0.25 mmol) of the product of step b) and 98 mg (130 µl, 0.76 mmol) N-ethyl diisopropylamine in 20 ml dichloromethane at room temperature. After 60 minutes the solvent was removed in a vacuum on a rotary evaporator and the product was purified by column chromatography (silica gel 60, Merck, mobile phase: dichloromethane:acetone 1:1 (v/v) containing 0.2% (v/v) triethylamine) (yield: 205 mg).

EXAMPLE 2

Oligonucleotide Synthesis

General Method for Synthesis of Dual Labeled Hydrolysis Probes

Oligonucleotide synthesis was performed in the 1 µmol range on an ABI 394 Synthesizer. Commercially available standard tac protected phosphoramidites from Proligo were used and chemicals for standard synthesis were obtained from Glen Research.

As solid phase BHQ2 CPG (Biosearch) was used in order to obtain 3' BHQ2 labeled oligonucleotides. The phosphoramidites from example 1a) and 1c) were filled in an appropriate bottle, diluted with anhydrous acetonitrile to a concentration of 100 µmol/l and attached to the extra position of the synthesizer. Manufactures default 1 µmol synthesis cycle was used. Coupling time for phosphoramidites 1a und 1c was extended to 5 min Synthesis of Dual Labeled Hydrolysis Probes Using 1c Removal of the oligonucleotides synthesized according to the method of a) from the solid support and deprotection was carried out with an aqueous, 33% (w/v) ammonia solution for two hours at room temperature. The solvent was removed in a vacuum. The residuum was dissolved in buffer A (aqueous, 0.1M triethylammonium acetate solution adjusted to pH 7.0). The (labeled) oligonucleotide was purified by reversed phase chromatography using an Oligo R3 column (4.6×50 mm) by using buffer A: aqueous, 0.1M triethylammonium acetate solution, pH 7.0 and buffer B: aqueous 0.1 M triethylammonium acetate solution pH 7.0 :acetonitrile 1:1 (v/v). The gradient comprises at a linear flow of 1 ml/min 2 minutes at 0% B and then in 45 minutes to 100%B. The obtained fractions of each 2 minutes size were analyzed by a HPLC with a diode array detector. Fractions with a purity of 90% or more and with absorption bands at 260, 450 and 579 nm were combined. The solvent was removed in a vacuum by using a vacuum centrifuge. The residuum was dissolved in double distilled water and then the solvent was removed again in a vacuum centrifuge. This procedure has been repeated three times. The final pellet was dissolved in water and was lyophilized.

Synthesis of a modified oligonucleotide by using the aminomodifier from example 1 a (diisopropyl-phosphoramidous acid 2-[bis-(4-methoxy-phenyl)-phenyl-methoxymethyl]-5-{5-methanesulfonylamino-3-[3-(2,2,2-trifluoro-acetylamino)-propyl]-indol-1-yl}-tetrahydro-furan-3-yl ester 2-cyano-ethyl and postlabeling Removal of the oligonucleotides synthesized according to the method of a) from the solid support and deprotection was carried out with an aqueous, 33% (w/v) ammonia solution for two hours at room temperature. The solvent was removed in a vacuum. The residuum was dissolved in 600 µl double distilled water and transferred into a microcentrifuge tube. 60 µl of sodium acetate buffer (3M, pH 8.5) were added. After the addition of 1.8 ml cold (4° C.) ethanol the mixture was stored at −15° C. for 3 h. The obtained solution was centrifuged at 10,000×g for 15 min. The supernatant was removed by decantation. The pellet was washed with 200 µl cold ethanol (4° C.). After centrifugation the supernatant was removed by decantation. The pellet was dissolved in 400 µl sodium borate buffer (0.1M, pH 8.5) and was labeled according to procedures known to a person skilled in the art. Accordingly a solution of 1 mg of a Coumarin dye NHS esters according to example 1b in DMF (1 ml) was added and the mixture was shaken for 15 h at room temperature. The solvent was removed in a high vacuum (1 mbar) using a rotary evaporator. Purification was performed as described above. With this method the following oligonucleotides were synthesized:

```
Coumarin 343 C3-methanesulfonylamino indole-
CACCAGATCCACGCCCT TGATGAGC   (SEQ ID NO: 01)-BHQ2
and Coumarin 343 C6-methanesulfonylamino indole-
CACCAGATCCACGCCCT TGATGAGC   (SEQ ID NO: 01)-BHQ2
```

Synthesis of an internally modified dual labeled probe by using the aminomodifier from example 1a (diisopropyl-phosphoramidous acid 2-[bis-(4-methoxy-phenyl)-phenyl-methoxymethyl]-5-{5-methanesulfonylamino-3-[3-(2,2,2-trifluoro-acetylamino)-propyl]-indol-1-yl}-tetrahydro-furan-3-yl ester 2-cyano-ethyl and postlabeling In difference to the procedure described above standard dT-CPG (Glen Research #20-2130-41) was used as solid phase and 5'-fluorescein phosphoramidite (6-FAM) from Biosearch (Cat no. BNS-5025-100) was used as 5'-label. For the postlabeling reaction I mg of 6-carboxytetramethyl-rhodamine succinimidyl ester (6-TAMRA-NHS-ester) (Invitrogen # C6123) was dissolved in 0.75 ml of acetonitrile and reacted overnight at room temperature with the aminomodified oligonucleotide of example 1 a) in 0.25 ml of sodium borate buffer (0.1M, pH 8.5). The double labeled oligonucleotide was purified by reversed phase chromatography using a PRP1-material (d=2 cm) column: Chromatography conditions: buffer A: 0.1M solution of triethylammonium acetate in water adjusted to pH 7.0 with 5% (v/v) acetonitrile; buffer B: 0.1 M triethylammonium acetate in water: acetonitrile 1:1 (v/v); gradient: from 0 to 40% B in 60 min. The obtained fractions were analyzed by HPLC with a diode array detector.

Fractions with purity of more than 90% and with absorption bands at 260, 494 and 558 nm were combined. The fractions from the peaks comprising the labeled oligonucleotide were collected and the solvent was removed using a vacuum centrifuge. The residuum was dissolved in double distilled water and the solvent was again removed using a vacuum centrifuge. This procedure was repeated three times. The resulting pellet was dissolved in water and lyophilized. With this method the following oligonucleotide was synthesized:

```
5'- (6-FAM) CCCGCCGGAGACTCCAACATTG (SEQ ID NO: 02)
(6-TAMRA-C3-methanesulfonylamino indole)TT -3'
```

MALDI-MS: M. W. [g/mol] calculated 8670.2; M. W. found 8669.65.

EXAMPLE 3

Detection of Viral Target DNA by Real-time PCR Using Hydrolysis Probes from Example 2

PCR was performed using a LightCycler® 480 instrument with the usual equipment. The PCR mix was prepared according to the recommendations of the manufacturer inserted to the generic PCR kit: LightCycler® 480 Probes Master.

Reagents:
LightCycler® 480 Probes Master
Oligonucleotides

```
forward primer
GCTCGAGTGCGAAAAAACGTTC          (SEQ ID NO: 03)

reverse primer
CGGGGCGCTCGGCTAAC               (SEQ ID NO: 04)

Probe Coumarin 343 - X -
CACCAGATCCACGCCCTTGATGAGC - BHQ2
X = C3- or C6-linker(SEQ ID NO: 01).
``` final concentrations of the primers: 0.3 µM, probe: 0.05 µM

Purified Target DNA

Instrument Protocol:

| Setup | | | |
|---|---|---|---|
| Detection Format | Filter Setting | Block Type | Reaction Volume |
| Hydrolysis Probe | Cyan 500 (450-500) | 384 | 20 µl |

| Programs | | |
|---|---|---|
| Program Name | Cycles | Analysis Mode |
| Denaturation | 1 | None |
| Amplification | 45 | Quantification |
| Cooling | 1 | None |

| Temperature Targets | | | | |
|---|---|---|---|---|
| Program | Target Temp. (° C.) | Acquis. Mode | Hold (mm:ss) | Ramp Rate (° C./s) |
| Denaturation | 95 | None | 05:00 | 4.8 |
| Amplification | 95 | None | 00:10 | 4.8 |
|  | 55 | Single | 00:25 | 2.5 |
|  | 72 | None | 00:05 | 4.8 |
| Cooling | 40 | None | 00:30 | 2.5 |

Figure 2:
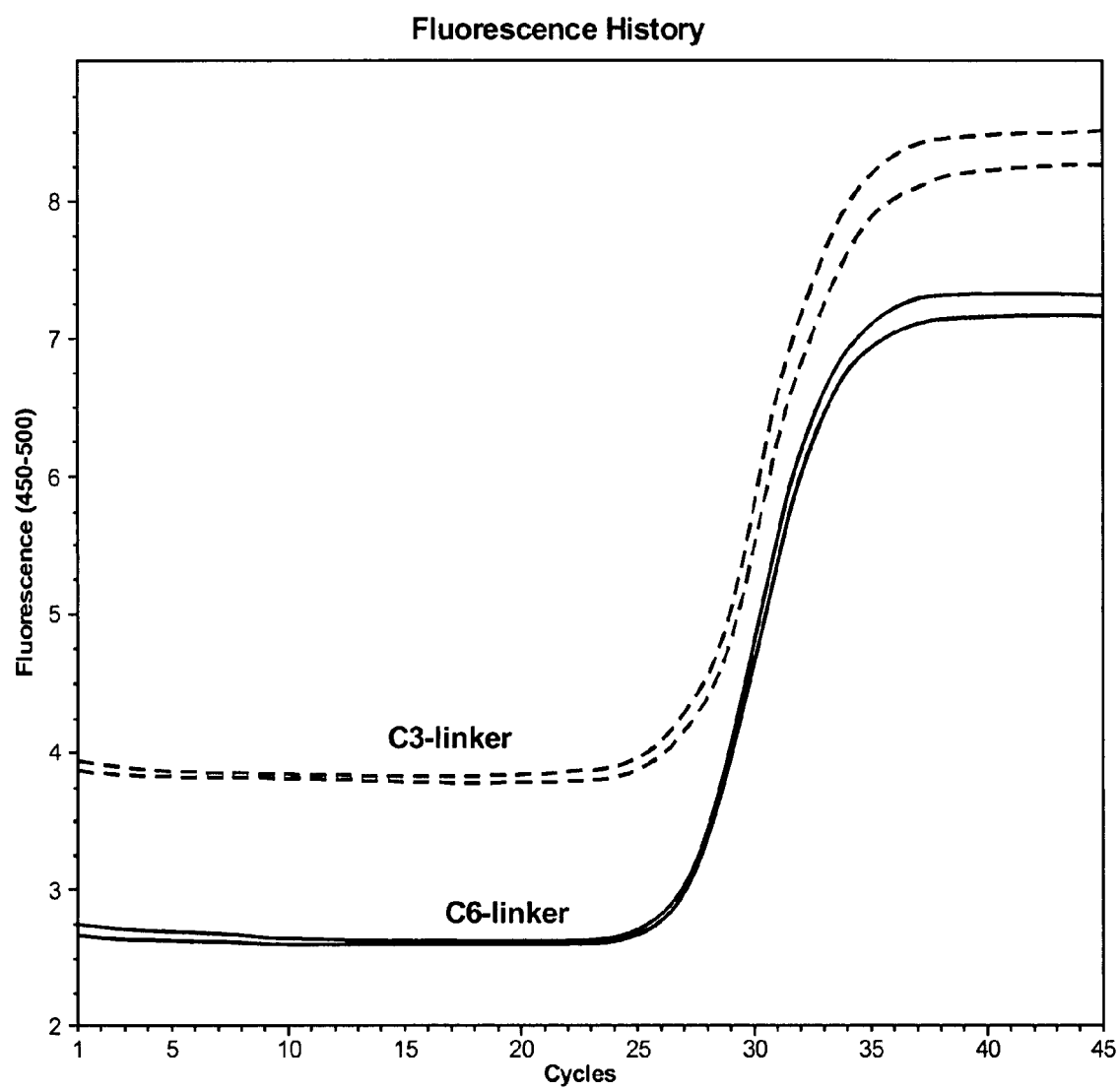
FIG. 2: Fluorescence change during nucleic acid amplification

Results:

Amplification of target DNA is monitored by fluorescence measurement of dequenched Cyan 500 (excitation at 450 nm, emission detection at 500 nm) (FIG. 2).

The signal at 500 nm increased during hydrolysis since the coumarin is cleaved during the PCR by the Taq polymerase. As could be seen from FIG. 2 the linker has an influence on signal increase and height, and therefore the fluorescence properties could be adapted to different applications. For Hydrolysis probe format its desirable to have a highly fluorescent reporter whereas for multiplexing with the Hybprobe format it could be of advantage if the FRET donor signal is weak.

---

What is claimed is:

1. A compound having the formula

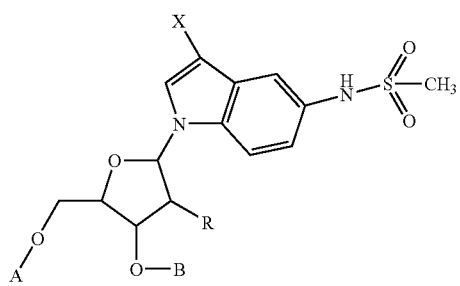

wherein

A and B are independent from each other and are independent from R and X, and A and B are selected from the group consisting of hydrogen, a protecting group, a solid phase with a linker, a phosphoramidite, an H-phosphonate, a triphosphate, a phosphate, and a chain of nucleotide residues, with the proviso that only A may be a triphosphate, with the proviso that if one of A or B is a phosphoramidite or an H-phosphonate, the other of A and B is a protective group and R is not OH, with the proviso that only one of A and B is a solid phase with a linker, R is selected from the group consisting of H, OH, O-alkyl, O-alkenyl, O-alkinyl, O-protective group, and F, and X is selected from the group consisting of a reactive group, a protected reactive group, a linker with a reactive group a linker with a protected reactive group, a signal entity, a protected signal entity, a linker with a signal entity, and a linker with a protected signal entity.

2. The compound of claim 1 wherein X is selected from the group consisting of a reactive group, a protected reactive group, a linker group, a protected linker group, and a signal entity.

3. The compound of claim 1 wherein R=H.

4. The compound of claim 1 wherein B is selected from the group consisting of a phosphoramidate group, an H-phosphonate, and a CPG and A is a protective group.

5. The compound of claim 1 wherein A is selected from the group consisting of a phosphoramidate group, an H-phosphonate, and a CPG and B is a protective group.

6. An oligonucleotide comprising a compound having the formula:

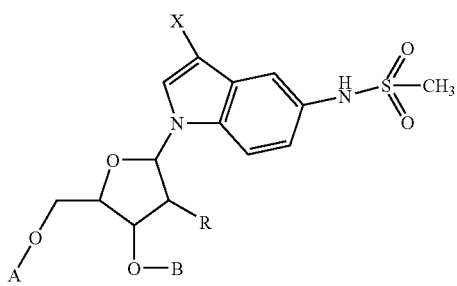

wherein

A and B are independent from each other and are independent from R and X, and A and B are selected from the group consisting of hydrogen, a protecting group, a solid phase with a linker, a phosphoramidite, an H-phosphonate, a triphosphate, a phosphate, and a chain of nucleotide residues, with the proviso that A but not B is a triphosphate, with the proviso that if one of A or B is a phosphoramidite or an H-phosphonate, the other of A and B is a protective group and R is not OH, with the proviso that only one of A and B is a solid phase with a linker, R is selected from the group consisting of H, OH, O-alkyl, O-alkenyl, O-alkinyl, O-protective group, and F, and X is selected from the group consisting of a reactive group, a protected reactive group, a linker with a reactive group, a linker with a protected reactive group, a signal entity, a protected signal entity, a linker with a signal entity, and a linker with a protected signal entity.

7. The oligonucleotide of claim 6 wherein said oligonucleotide further comprises a second compound having said formula.

8. The oligonucleotide of claim 6 wherein said oligonucleotide comprises at least two signal entities.

9. The oligonucleotide of claim 6 wherein said signal entity is a fluorescent entity.

10. A method for synthesis of the oligonucleotide of claim 6 comprising the steps of
providing a nucleotide,
elongating the nucleotide, and
incorporating during the elongation a compound having the formula

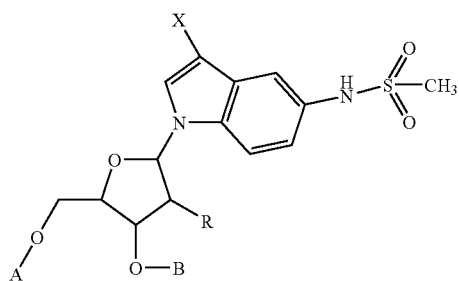

wherein
A is a protecting group and B is selected from the group consisting of a phosphoramidate group, an H-phosphonate, and a CPG, R is selected from the group consisting of H, OH, O-alkyl, O-alkenyl, O-alkinyl, O-protective group, and F, and X is selected from the group consisting of a reactive group, a protected reactive group, a linker with a reactive group, a linker with a protected reactive group, a signal entity, a protected signal entity, a linker with a signal entity, and a linker with a protected signal entity, thereby forming said oligonucleotide.

11. The method of claim 10
wherein
X is a reactive group or a linker with a reactive group, and wherein the method further comprises the step of
coupling a signal entity to said reactive group.

12. A hybridization probe comprising a compound having the formula:

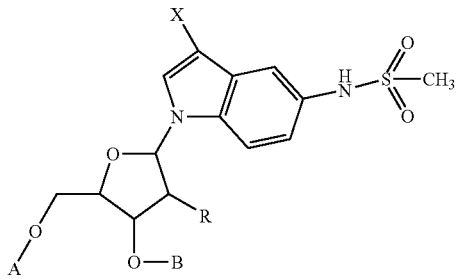

wherein
A and B are independent from each other and are independent from R and X, and A and B are selected from the group consisting of hydrogen, a protecting group, a solid phase with a linker, a phosphoramidite, an H-phosphonate, a triphosphate, a phosphate, and a chain of nucleotide residues, with the proviso that A but not B is a triphosphate, with the proviso that if one of A or B is a phosphoramidite or an H-phosphonate, the other of A and B is a protective group and R is not OH, with the proviso that only one of A and B is a solid phase with a linker, R is selected from the group consisting of H, OH, O-alkyl, O-alkenyl, O-alkinyl, O-protective group, and F, and X is selected from the group consisting of a reactive group, a protected reactive group, a linker with a reactive group, a linker with a protected reactive group, a signal entity, a protected signal entity, a linker with a signal entity, and a linker with a protected signal entity.

* * * * *

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caccagatcc acgcccttga tgagc                                            25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 2
cccgccggag actccaacat tg                                                22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctcgagtgc gaaaaaacgt tc                                                22

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggggcgctc ggctaac                                                      17
```